United States Patent
Vincent et al.

(10) Patent No.: US 12,259,450 B2
(45) Date of Patent: Mar. 25, 2025

(54) SYSTEMS, ASSEMBLIES, AND METHODS OF FABRICATION OF RADIO-FREQUENCY COIL ASSEMBLIES OF A MAGNETIC RESONANCE SYSTEM

(71) Applicant: GE Precision Healthcare LLC, Wauwatosa, WI (US)

(72) Inventors: Jana M. Vincent, Aurora, OH (US); Fraser J. L. Robb, Aurora, OH (US)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 185 days.

(21) Appl. No.: 18/313,043

(22) Filed: May 5, 2023

(65) Prior Publication Data
US 2024/0369656 A1   Nov. 7, 2024

(51) Int. Cl.
G01R 33/34   (2006.01)
A61B 5/055   (2006.01)
G01R 33/385  (2006.01)

(52) U.S. Cl.
CPC ........ *G01R 33/34092* (2013.01); *A61B 5/055* (2013.01); *G01R 33/34084* (2013.01); *G01R 33/385* (2013.01)

(58) Field of Classification Search
CPC ........ G01R 33/34092; G01R 33/34084; G01R 33/385; G01R 33/34007; A61B 5/055
See application file for complete search history.

(56) References Cited

U.S. PATENT DOCUMENTS

| | | | |
|---|---|---|---|
| 2022/0252684 A1 | 8/2022 | Rispoli | |
| 2023/0368971 A1 | 11/2023 | Lu | |
| 2024/0369655 A1* | 11/2024 | Vincent | A61B 5/055 |

FOREIGN PATENT DOCUMENTS

| | | | |
|---|---|---|---|
| DE | 102008051945 A1 | 5/2009 | |
| EP | 3889631 A1 | 10/2021 | |

OTHER PUBLICATIONS

English Translation of EP3243946-A1, Becker et al., Textile Tool, Use of the Textile Tool and Method for Producing the Same (Year: 2017).*
"Applique Foot AP for Janome 9mm Machines", YouTube Video, dated Feb. 15, 2013, accessed online at URL: https://www.youtube.com/watch v=-QWE7HyAers.

(Continued)

Primary Examiner — G. M. A Hyder
(74) Attorney, Agent, or Firm — Armstrong Teasdale LLP

(57) ABSTRACT

A method of fabricating a stretchable RF coil assembly of an MR system using a sewing machine is provided. The method includes providing a sewing accessory assembly. The sewing accessory assembly includes a substrate holder including an inner hoop and an outer hoop. The method also includes assembling a former and a stretchable substrate with the substrate holder by coupling sides of the former and sides of the stretchable substrate between the inner hoop and the outer hoop. The method further includes coupling the assembled substrate holder with a sewing machine, and assembling an RF coil assembly by sewing a pattern of a fiber conductor on the stretchable substrate.

20 Claims, 19 Drawing Sheets

(56) References Cited

OTHER PUBLICATIONS

"Brother Universal Sewing Machine Needles (5 Piece)", Walmart Product Webpage, accessed online on Apr. 26, 2023 at URL: https://www.walmart.com/ip/Brother-Universal-Sewing-Machine-Needles-5-Piece/51741793wmlspartner=wlpa selectedSellerId= 0wl13=5313 adid=2222222227751741793_117755028669_ 12420145346 wmlspartner=wmtlabs wl0= wl1=g wl2=cwl3= 501107745824 wl4=pla-294505072980 wl5=9022943 wl6= wl7= wl8= wl9-pla wl10=8175035 wl11=local wl12=51741793 wl13= 5313 veh=sem_LIA.

"Janome Applique Foot For 9mm Machines", Amazon Product Webpage, acessed online on Apr. 25, 2023 at URL: https://www.amazon.com/Janome-Applique-Foot-9mm-Machines/dp/B00MGVRD24/ref=asc_df_B00MGVRD24/tag=hyprod-20 linkCode= df0 hvadid=196246093157 hvpos= hvnetw=g hvrand= 4056505097726588721 hvpone=hvptwo= hvqmt= hvdev=c hvdvcmdl= hvlocint= hvlocphy=9022943 hvtargid=pla-316024472388 psc=1.

"Round Bead Foot", YouTube Video, dated Oct. 30, 2021, accessed online at URL: https://www.youtube.com/watchv=xYs4cZaOh-c.

"Sew Tech Embroidery Hoops for Brother SE600 PE550D SE700 PE535 SE400 PE525 PE540D PE500 SE625 SE425 Innovis Babylock Brother Embroidery Machine Hoop (3in1 Set)", Amazon Product Webpage, accessed online on Apr. 26, 2023 at URL: https://www.amazon.com/Embroidery-Brother-Innovis-Babylock-Machine/dp/B07YVJ14K7/ref=asc_df_B07YVJ14K7/tag= linkCode=df0 hvadid= 385122001650 hvpos= hvnetw=g hvrand=17704998920789097311 hvpone= hvptwo= hvqmt= hvdev=c hvdvcmdl= hvlocint= hvlocphy= 9022943 hvtargid=pla-833193096409 ref= adgrpid=78285594373 th=1.

"SINGER Beading Foot", Joann Product Webpage, accessed online on Apr. 25, 2023 at URL: https://www.joann.com/singer-beading-foot/18429068.htmlgclid=EAIaIQobChMIrcHUz4bF_gIVGQytBh34fQ-HEAQYASABEgKkZfD_BwE.

Agir et al., "A Wearable and Flexible 23Na Transmit/Receive Breast Coil at 3T", No. 4104, Proc. Intl. Soc. Mag. Reson. Med. 28 (2020).

Corea et al., "Screen-printed flexible MRI receive coils", Nat Commun 7, 10839 (2016), published Mar. 10, 2016, DOI: https://doi.org/10.1038/ncomms10839.

Motovilova et al., "Stretchable self-tuning MRI receive coils based on liquid metal technology (LiquiTune)", Sci Rep 11, 16228 (2021), published Aug. 10, 2021, DOI: https://doi.org/10.1038/s41598-021-95335-6.

Nordmeyer-Massner et al., "MR imaging of healthy knees in varying degrees of flexion using a stretchable coil array provides comparable image quality compared to a standard knee coil array", Eur J Radiol, Mar. 2016;85(3):518-23, doi: 10.1016/j.ejrad.2015.12.004, Epub Dec. 18, 2015.

Port et al., "Detector clothes for MRI: A wearable array receiver based on liquid metal in elastic tubes", Sci Rep 10, 8844 (2020), published Jun. 1, 2020, DOI: https://doi.org/10.1038/s41598-020-65634-5.

Port et al., "Elastomer coils for wearable MR detection", vol. 85, Issue 5, May 2021, pp. 2882-2891, First published Jan. 12, 2021, DOI: https://doi.org/10.1002/mrm.28662.

Port et al., "Towards wearable MR detection: A stretchable wrist array with on-body digitization", No. 0017, Proc. Intl. Soc. Mag. Reson. Med. 26 (2018).

Varga et al., "Adsorbed Eutectic GaIn Structures on a Neoprene Foam for Stretchable MRI Coils", Adv Mater. Nov. 2017; 29(44), First published Oct. 13, 2017, doi: 10.1002/adma.201703744.

Vincent et al., "Twenty-channel, Highly-stretchable, Overlapped, Receive (THOR) Array", May 7-12, 2022, Joint Annual Meeting ISMRM-ESMRMB, ISMRT 31st Aannual Meeting.

\* cited by examiner

SYSTEMS, ASSEMBLIES, AND METHODS OF FABRICATION OF RADIO-FREQUENCY COIL ASSEMBLIES OF A MAGNETIC RESONANCE SYSTEM

BACKGROUND

The field of the disclosure relates generally to a magnetic resonance (MR) system, and more particularly, to radio frequency (RF) coil assemblies for an MR system.

Magnetic resonance imaging (MRI) has proven useful in diagnosis of many diseases. MRI provides detailed images of soft tissues, abnormal tissues such as tumors, and other structures, which cannot be readily imaged by other imaging modalities, such as computed tomography (CT). Further, MRI operates without exposing patients to ionizing radiation experienced in modalities such as CT and x-rays.

In MRI, an RF coil assembly is used to detect MR signals emitted from a subject and thus is a key component of an MR system. Known systems, assemblies, and methods of fabrication of RF coil assemblies are disadvantaged in some aspects and improvements are desired.

BRIEF DESCRIPTION

In one aspect, a method of fabricating a radio-frequency (RF) coil assembly of a magnetic resonance (MR) system using a sewing machine is provided. The method includes providing a sewing accessory assembly, the sewing accessory assembly including a substrate holder. The substrate holder includes an inner hoop, an outer hoop, and one or more coil loop supports configured to be coupled with the inner hoop and be positioned within the inner hoop. The method also includes coupling an RF coil loop with one of the one or more coil loop supports, and assembling a substrate with the substrate holder by securing the substrate between the inner hoop and the outer hoop. The method further includes coupling the assembled substrate holder with a sewing machine and assembling an RF coil assembly by sewing stitches to attach the RF coil loop with the substrate.

In another aspect, a method of fabricating a stretchable RF coil assembly of an MR system using a sewing machine is provided. The method includes providing a sewing accessory assembly. The sewing accessory assembly includes a substrate holder including an inner hoop and an outer hoop. The method also includes assembling a former and a stretchable substrate with the substrate holder by coupling sides of the former and sides of the stretchable substrate between the inner hoop and the outer hoop. The method further includes coupling the assembled substrate holder with a sewing machine, and assembling an RF coil assembly by sewing a pattern of a fiber conductor on the stretchable substrate.

In one more aspect, a sewing accessory assembly of a sewing machine for fabricating an RF coil assembly of an MR system is provided. The sewing accessory assembly includes a needle defining an eye, the needle further including a lining positioned around the eye and configured to reduce fraying of a fiber conductor.

BRIEF DESCRIPTION OF DRAWINGS

Non-limiting and non-exhaustive embodiments are described with reference to the following figures, wherein like reference numerals refer to like parts throughout the various drawings unless otherwise specified.

DETAILED DESCRIPTION

Figure 1:
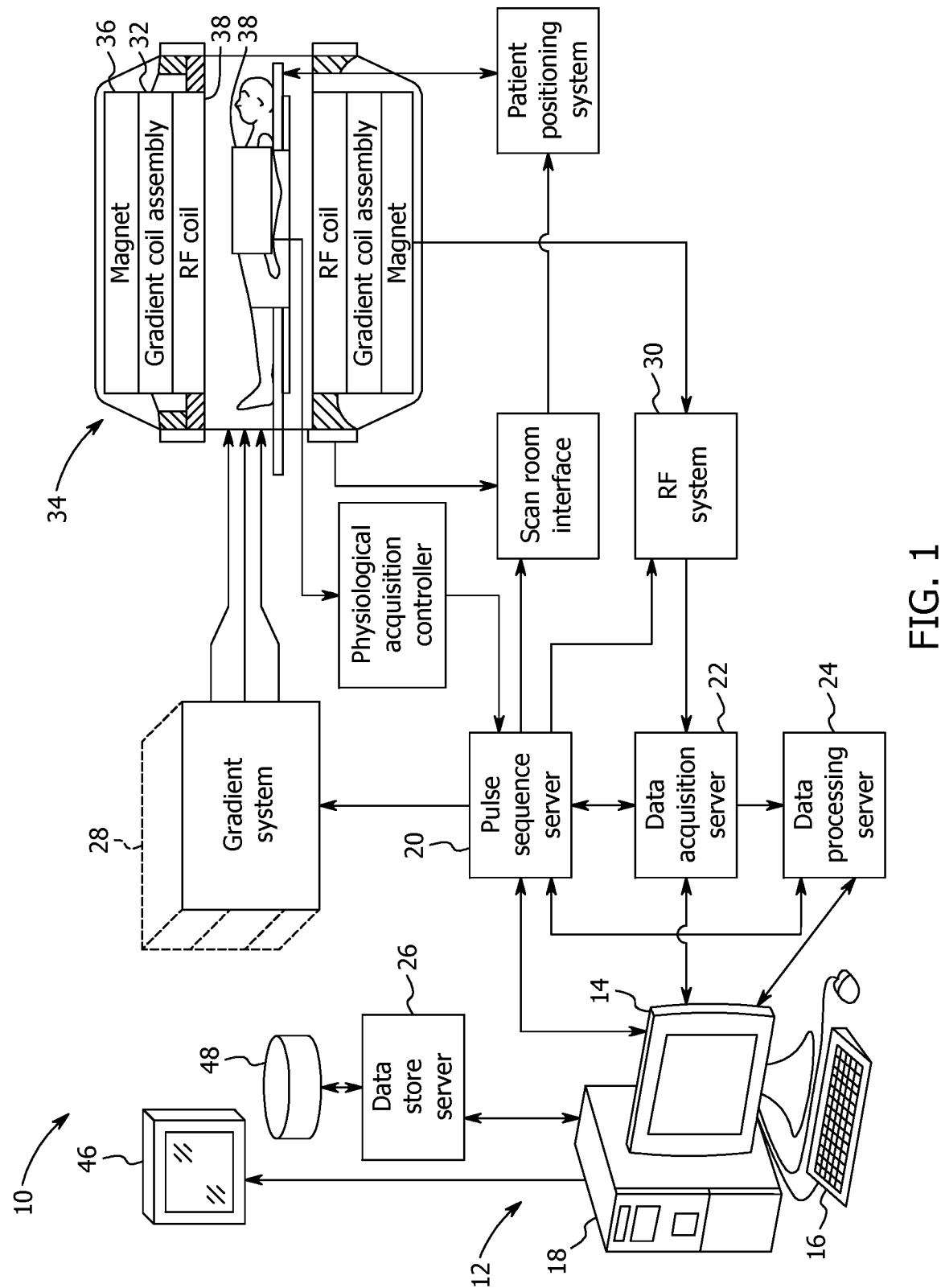
FIG. 1 is a block diagram of a magnetic resonance (MR) system.

The disclosure includes systems, assemblies, and methods of fabrication of radio frequency (RF) coil assemblies for use in magnetic resonance (MR) systems for scanning a subject. As used herein, a subject is a human, an animal, a phantom, or any object scanned by a medical imaging system. MR imaging is described as an example only. The assemblies, systems, and methods described herein may be used for MR spectroscopy. MR systems are described as examples only. The systems, assemblies, and methods described herein may be used for medical imaging systems other than MR systems, such as positron emission tomography (PET)-MR systems. RF coil assemblies may also be used in transducers of MR guided focused ultrasound surgery (MRgfUS) systems. Conductive leads may also be used in electroencephalography (EEG). Method aspects of assembling and using the RF coil assemblies will be in part apparent and in part explicitly discussed in the following description.

RF coil loops may be stretchable by coil loops being coupled with stretchable substrate that exhibits viscoelasticity, and coil loops being in a nonlinear pattern such that coil loops are stretched along with the substrate and dimensions of coil loops may be changed in multiple directions. Being stretchable is when the dimensions of the coil loop may be changed by applying force in one or more directions. Stretchable RF coils are advantageous in conforming with anatomy of the subject, thereby providing increased signal to noise ratio (SNR). Stretchable RF coils also provide increased subject comfort.

Fabricating RF coils, especially stretchable RF coils, using known methods is tedious and time consuming. Known fabrication methods are largely manual, which are prone to errors and relatively slow, and therefore unsatisfactory for large-scale industry production. In known methods, sewing of RF coil loops with a substrate has a high rate of defects, where the coil loop is punctured by needles, reducing the insulation of coil loops. In one known method, a coil loop of braided wires is knitted onto a stretchable substrate. The coil loop, however, may only be stretched or deformed in one direction due to the constraint from knitting and the braided wires. Further, knitting does not provide flexibility in designing the pattern of coil loops.

The methods and assemblies described herein overcome the above described problems in known methods. The methods and assemblies described herein include accessory assemblies to enable fabrication of RF coil assemblies using a sewing machine. As used herein, a sewing machine is a machine that drives a needle to produce stitches on a material, and may be a regular sewing machine, an embroidery machine, or a combination of both. The speed of fabrication is increased. For example, fabricating a coil loop may take a few minutes with the methods, systems, and assemblies described herein, as compared to hours in known methods. Fabricating RF coil assemblies using a sewing machine as described herein is advantageous than other known methods in providing RF coil assemblies with increased quality, where the sewing machine has more precise and finer control of the movement, the pattern, and/or attachment of the stretchable material with the coil loop, during the fabrication process than a human or in other methods. The systems, assemblies, and methods described herein enable industry-scale fabrication of RF coil assemblies with reduced time and increased quality. Besides automizing the fabrication, the systems, assemblies, and methods are advantageous in providing customized fabrication of RF coil assemblies. The designs of the RF coil loops may be input into the sewing machine. To customize the design, only design files need to be modified.

In fabricating a stretchable RF coil, sagging or uneven stretching of the substrate is challenging. Systems, assemblies, and methods described herein are advantageous in reducing sagging of the substrate during sewing from the pulling and tucking of the needle. A substrate holder is used to provided tension on the substrate. Sagging is further reduced by using a water-soluble former. Former is removed by being dissolved in water, without causing changes to coil loops. The material of the former is chosen such that the former does not produce detectable MR signals, thereby not affecting the performance of the RF coil assembly even if the former is not completely removed from assembled coil loops. Sagging may be further reduced by using a substrate holder that provides support from coil loop supports and a former may not be needed, thereby saving time, material, and labor.

In MR imaging (MRI), a subject is placed in a magnet. When the subject is in the magnetic field generated by the magnet, magnetic moments of nuclei, such as protons, attempt to align with the magnetic field but precess about the magnetic field in a random order at the nuclei's Larmor frequency. The magnetic field of the magnet is referred to as B0 and extends in the longitudinal or z direction. In acquiring an MR image, a magnetic field (referred to as an excitation field B1), which is in the x-y plane and near the Larmor frequency, is generated by an RF coil and may be used to rotate, or "tip," the net magnetic moment Mz of the nuclei from the z direction to the transverse or x-y plane. A signal, which is referred to as an MR signal, is emitted by the nuclei, after the excitation signal B1 is terminated. To use the MR signals to generate an image of a subject, magnetic field gradient pulses ($G_x$, $G_y$, and $G_z$) are used. The gradient pulses are used to scan through the k-space, the space of spatial frequencies or inverse of distances. A Fourier relationship exists between the acquired MR signals and an image of the subject, and therefore the image of the subject can be derived by reconstructing the MR signals.

FIG. 1 illustrates a schematic diagram of an example MR system 10. In the example embodiment, MR system 10 includes a workstation 12 having a display 14 and a keyboard 16. Workstation 12 includes a processor 18, such as a commercially available programmable machine running a commercially available operating system. Workstation 12 provides an operator interface that allows scan prescriptions to be entered into MR system 10. Workstation 12 is coupled to a pulse sequence server 20, a data acquisition server 22, a data processing server 24, and a data store server 26. Workstation 12 and each server 20, 22, 24, and 26 communicate with each other.

In the example embodiment, pulse sequence server 20 responds to instructions downloaded from workstation 12 to operate a gradient system 28 and an RF system 30. The instructions are used to produce gradient and RF waveforms in MR pulse sequences. An RF coil assembly 38 and a gradient RF coil assembly 32 are used to perform the prescribed MR pulse sequence. RF coil assembly 38 may be a whole body RF coil. RF coil assembly 38 may also be a local RF coil assembly 38 that may be placed in proximity to the anatomy to be imaged, or a coil array that includes a plurality of coils.

In the example embodiment, gradient waveforms used to perform the prescribed scan are produced and applied to gradient system 28, which excites gradient coils in gradient RF coil assembly 32 to produce the magnetic field gradients $G_x$, $G_y$, and $G_z$ used for position-encoding MR signals. Gradient RF coil assembly 32 forms part of a magnet assembly 34 that also includes a polarizing magnet 36 and RF coil assembly 38.

In the example embodiment, RF system 30 includes an RF transmitter for producing RF pulses used in MR pulse sequences. The RF transmitter is responsive to the scan prescription and direction from pulse sequence server 20 to produce RF pulses of a desired frequency, phase, and pulse amplitude waveform. The generated RF pulses may be applied to RF coil assembly 38 by RF system 30. Responsive MR signals detected by RF coil assembly 38 are received by RF system 30, amplified, demodulated, filtered, and digitized under direction of commands produced by pulse sequence server 20. RF coil assembly 38 is described as a transmit and receive coil such that RF coil assembly 38 transmits RF pulses and detects MR signals. In one embodiment, MR system 10 may include a transmit RF coil that transmits RF pulses and a separate receive coil that detects MR signals. A transmission channel of RF system 30 may be connected to an RF transmit coil and a receiver channel may be connected to a separate RF receive coil. Often, the transmission channel is connected to the whole body RF coil assembly 38 and each receiver section is connected to a separate local RF coil.

In the example embodiment, RF system 30 also includes one or more RF receiver channels. Each RF receiver channel includes an RF amplifier that amplifies the MR signal received by RF coil assembly 38 to which the channel is connected, and a detector that detects and digitizes the I and Q quadrature components of the received MR signal. The magnitude of the received MR signal may then be determined as the square root of the sum of the squares of the I and Q components as in Eq. (1) below:

$$M = \sqrt{I^2 + Q^2} ; \qquad (1)$$

and the phase of the received MR signal may also be determined as in Eq. (2) below:

$$\varphi = \tan^{-1}\left(\frac{Q}{I}\right). \qquad (2)$$

In the example embodiment, the digitized MR signal samples produced by RF system 30 are received by data acquisition server 22. Data acquisition server 22 may operate in response to instructions downloaded from workstation 12 to receive real-time MR data and provide buffer storage such that no data is lost by data overrun. In some scans, data acquisition server 22 does little more than pass the acquired MR data to data processing server 24. In scans that need information derived from acquired MR data to control further performance of the scan, however, data acquisition server 22 is programmed to produce the needed information and convey it to pulse sequence server 20. For example, during prescans, MR data is acquired and used to calibrate the pulse sequence performed by pulse sequence server 20. Also, navigator signals may be acquired during a scan and used to adjust the operating parameters of RF system 30 or gradient system 28, or to control the view order in which k-space is sampled.

In the example embodiment, data processing server 24 receives MR data from data acquisition server 22 and processes it in accordance with instructions downloaded from workstation 12. Such processing may include, for example, Fourier transformation of raw k-space MR data to produce two or three-dimensional images, the application of filters to a reconstructed image, the performance of a back-projection image reconstruction of acquired MR data, the generation of functional MR images, and the calculation of motion or flow images.

In the example embodiment, images reconstructed by data processing server 24 are conveyed back to, and stored at, workstation 12. In some embodiments, real-time images are stored in a database memory cache (not shown in FIG. 1), from which they may be output to operator display 14 or a display 46 that is located near magnet assembly 34 for use by attending physicians. Batch mode images or selected real time images may be stored in a host database on disc storage 48 or on a cloud. When such images have been reconstructed and transferred to storage, data processing server 24 notifies data store server 26. Workstation 12 may be used by an operator to archive the images, produce films, or send the images via a network to other facilities.

During a scan, interfacing cables may be used to transmit signals between RF coil assembly 38 and other aspects of MR system 10 (e.g., RF system 30, data acquisition server 22, and pulse sequence server 20), for example to control the RF coils and/or to receive signals from the RF coils. As described above, the RF coil assembly 38 may be a transmit coil that transmits RF excitation signals, or a receive coil that receives the MR signals emitted by the subject. In an example, the transmit and receive coils are a single mechanical and electrical structure or array of structures, with transmit/receive mode switchable by auxiliary circuitry. In other examples, a transmit coil and a receive coil may be independent structures that are physically coupled to each other via the RF system 30. For enhanced image quality, however, a receive coil is desirable to be mechanically and electrically isolated from the transmit coil. In such cases, the receive coil in the receive mode is electromagnetically coupled to and resonant with an RF "echo" that is stimulated by the transmit coil. On the other hand, during a transmit mode, the receive coil is electromagnetically decoupled from and therefore not resonant with the transmit coil, during transmission of the RF signal. Such decoupling averts a potential problem of noise produced within the auxiliary circuitry when the receive coil couples to the full power of the RF signal.

A traditional receive coil for MR includes several conductive intervals joined between themselves by capacitors. By adjusting the capacitors' values, the impedance of the RF coil may be brought to its minimal value, usually characterized by a low resistance. At a resonant frequency, stored magnetic and electric energy alternate periodically. Each conductive interval, due to its length and width, possesses a certain self-capacitance, where electric energy is periodically stored as static electricity. The distribution of this electricity takes place over the entire conductive interval length in the order of 5-15 cm, causing similar range electric dipole field. In proximity of a large dielectric load, self-capacitance of the intervals change, resulting in detuning of the coil. In case of a lossy dielectric, dipole electric field causes Joule dissipation characterized by an increased overall resistance observed by the coil.

Traditional RF coils may include acid etched copper traces or loops on printed circuit boards (PCBs) with lumped electronic components (e.g., capacitors, inductors, baluns, and resisters), matching circuitry, decoupling circuitry, and pre-amplifiers. Such a configuration is typically bulky, heavy, and rigid, and requires relatively strict placement of the coils relative to each other in an array to prevent coupling interactions among coil elements that may degrade image quality. As such, traditional RF coils and RF coil arrays lack flexibility and therefore may not conform to subject anatomy, degrading imaging quality and subject comfort.

Figure 2A:
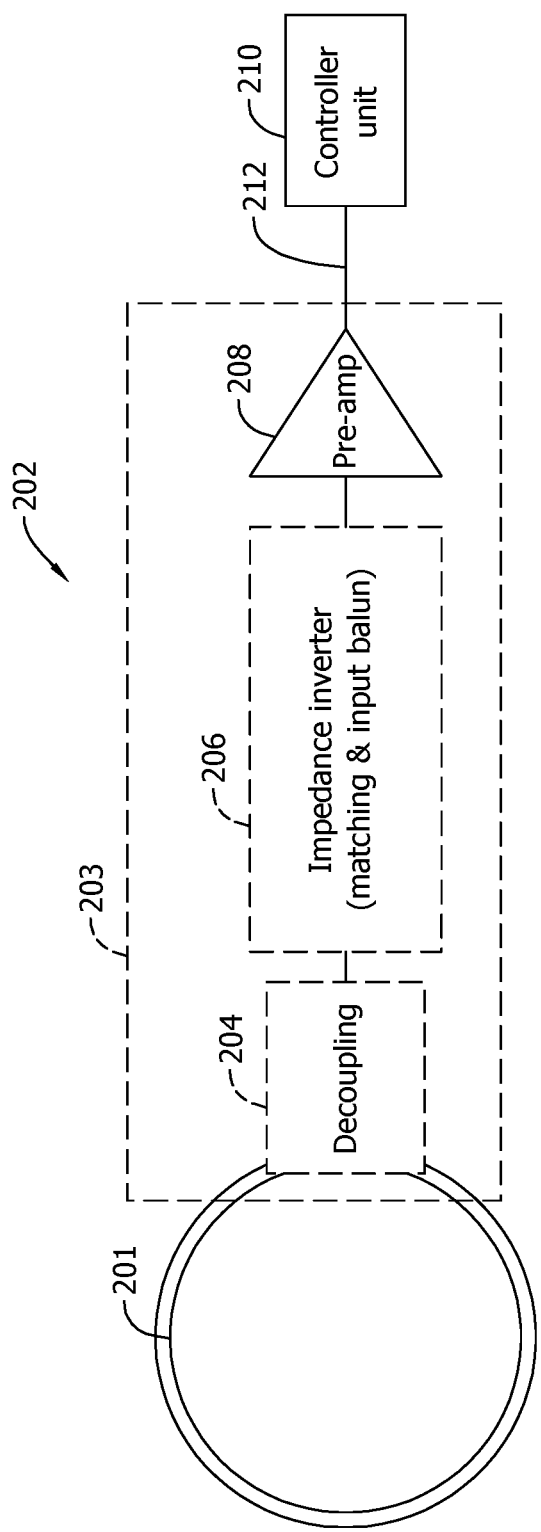
FIG. 2A is a block diagram of an example radio-frequency (RF) coil assembly.

FIG. 2A is a block diagram of an example RF coil 202. In the example embodiment, RF coil 202 includes coil loop 201 coupled to a controller unit 210 via a coupling electronics portion 203 and a coil-interfacing cable 212. Coil loop 201 is formed by a fiber conductor 220-*f* (FIG. 3B described later) or a wire conductor 220-*w* (FIGS. 8B and 8C described later). The length and the design of coil loop 201 is varied to achieve a select distributed capacitance (DCAP), and accordingly, a select resonance frequency. DCAP, as used herein, represents a capacitance exhibited between conductors that grows evenly and uniformly along the length of the conductors and is void of discrete or lumped capacitive components and discrete or lumped inductive components. In one example, the RF coil may be a surface receive coil, which may be single- or multi-channeled. RF coil 202 may operate at one or more frequencies in MR system 10. Coil-interfacing cable 212 may be a coil-interfacing cable extending between coupling electronics portions 203 or between an RF coil assembly and other components of MR system 10 such as RF system 30.

In the example embodiment, coupling electronics portion 203 may be coupled to coil loop 201 of RF coil 202. Coupling electronics portion 203 may include a decoupling circuit 204, impedance inverter circuit 206, and a pre-amplifier 208. Decoupling circuit 204 may effectively decouple the RF coil during a transmit operation. Typically, RF coil 202 in the receive mode may be positioned adjacent a body of a subject being imaged by MR system 10 in order to receive echoes of the RF signal transmitted during the transmit mode. If RF coil 202 is not used for transmission, RF coil 202 is decoupled from the RF transmit coil such as the RF body coil when the RF transmit coil is transmitting the RF signal. The decoupling of the receive coil from the transmit coil may be achieved using resonance circuits and PIN diodes, microelectromechanical systems (MEMS) switches, or another type of switching circuitry. The switching circuitry may activate detuning circuits operatively connected to RF coil 202.

In the example embodiment, the impedance inverter circuit 206 may form an impedance matching network between RF coil 202 and pre-amplifier 208. Impedance inverter circuit 206 is configured to transform a coil impedance of RF coil 202 into an optimal source of impedance for pre-amplifier 208. The impedance inverter circuit 206 may include an impedance matching network and an input balun. Pre-amplifier 208 receives MR signals from corresponding RF coil 202 and amplifies the received MR signals. In one example, the pre-amplifier may have a low input impedance that is configured to accommodate a relatively high blocking or source impedance. Coupling electronics portion 203 may be packaged in a small PCB with a surface area of approximately 2 cm² or smaller. The PCB may be protected with a conformal coating or an encapsulating resin.

Coil-interfacing cable 212 may be used to transmit signals between the RF coils and other components of MR system 10. The coil interfacing cables may be disposed within the bore or imaging space of MR system 10. In MR systems, coil-interfacing cables 212 may support transmitter-driven common-mode currents, which may in turn create field distortions and/or unpredictable heating of components. Typically, common-mode currents are blocked by using baluns. Baluns or common-mode traps provide high common-mode impedances, which in turn reduces the effect of transmitter-driven currents.

Figure 2B:
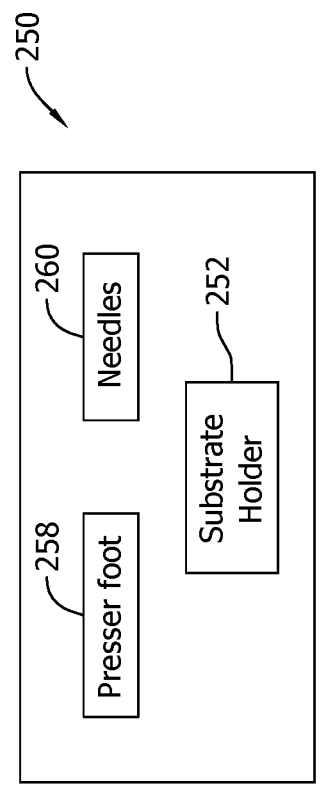
FIG. 2B is an example sewing accessory assembly for fabricating an RF coil assembly.
Figure 2C:
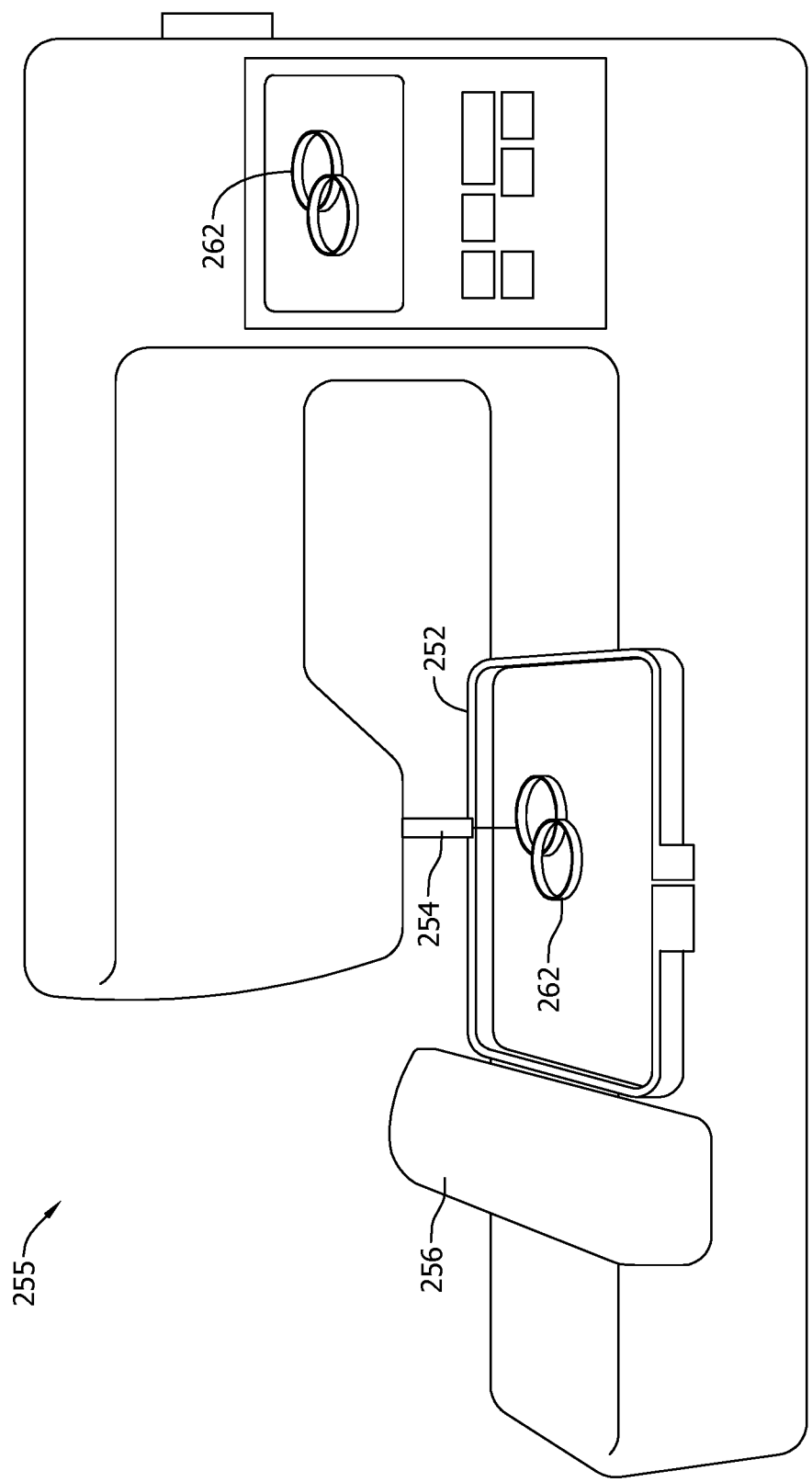
FIG. 2C shows a sewing machine.

FIG. 2B is a schematic diagram of an example sewing accessory assembly 250. FIG. 2C shows a sewing machine. In the example embodiment, sewing accessory assembly 250 includes a substrate holder 252 configured to be used on a sewing machine 255. Substrate holder 252 is configured to couple with an embroidery hoop coupler 256 of sewing machine 255. Sewing accessory assembly 250 may further include a presser foot 258. Sewing accessory assembly 250 may also include needles 260. Individual components and subparts of individual components may be fabricated with additive manufacturing.

Figure 3A:
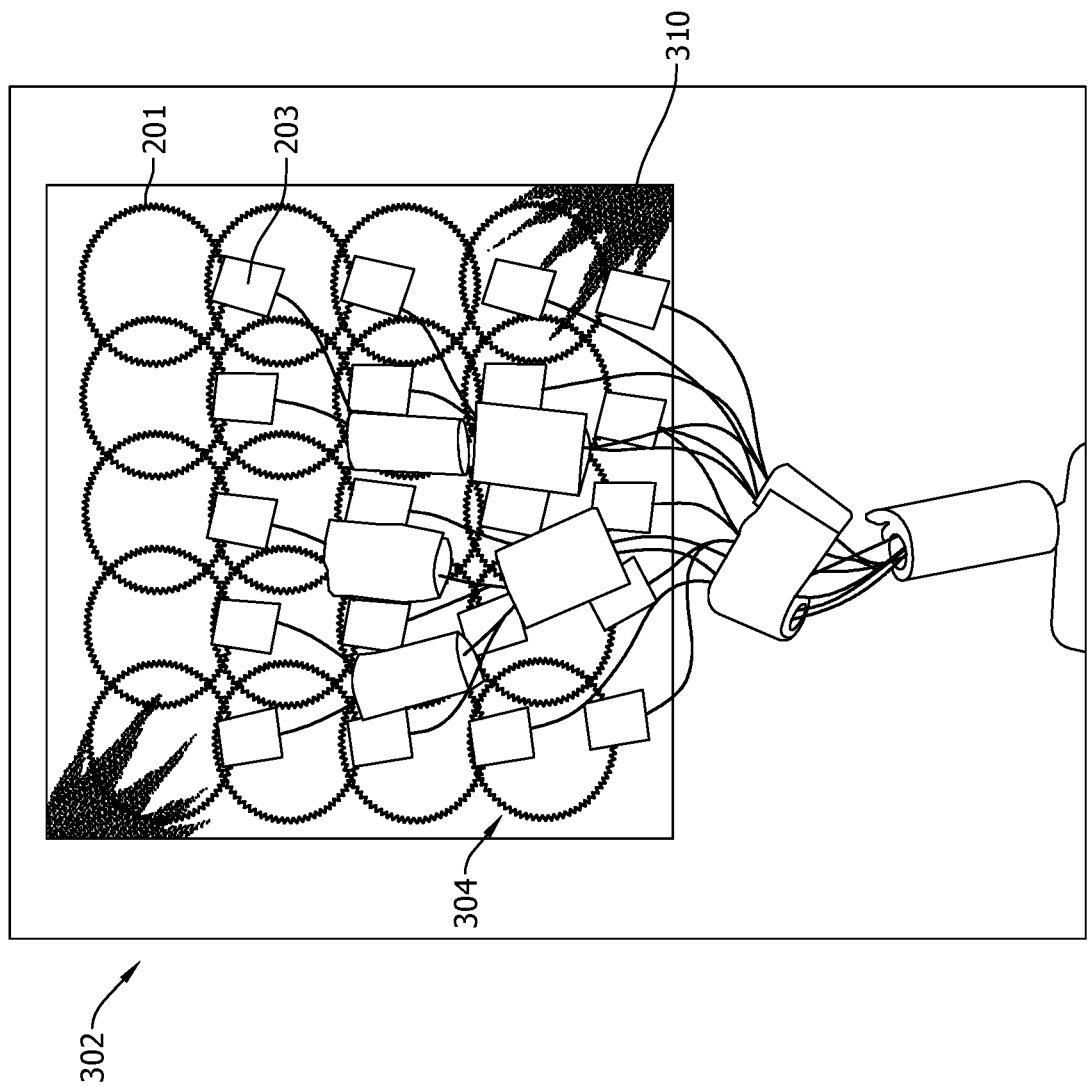
FIG. 3A shows an example RF coil assembly including coil loops fabricated with fiber conductors.
Figure 3B:
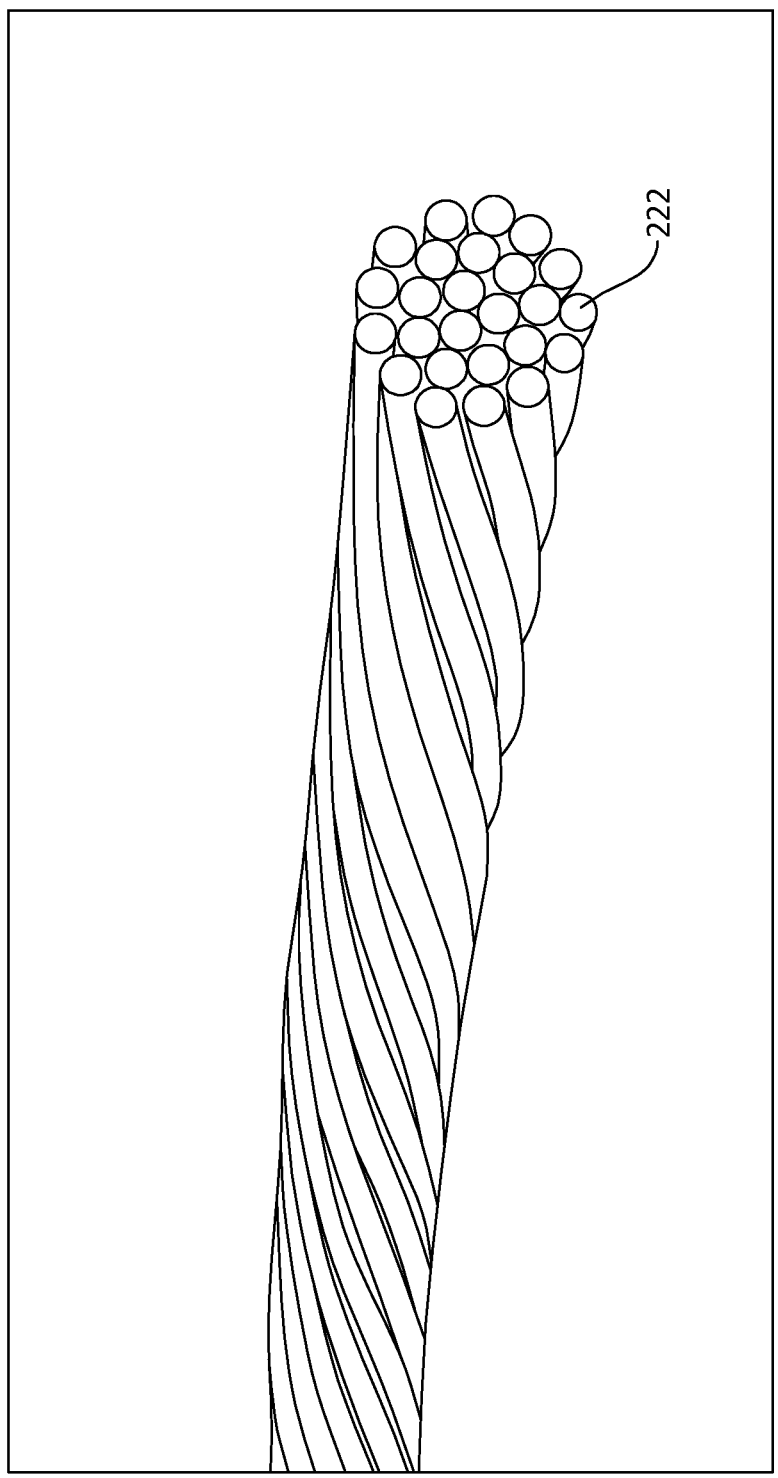
FIG. 3B is a schematic diagram showing a fiber conductor.
Figure 3D:
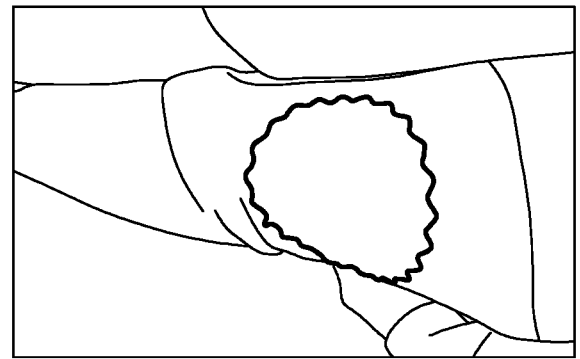
FIG. 3D illustrates the coil loop shown in FIG. 3C when being placed on an anatomy of a subject.
Figure 3C:
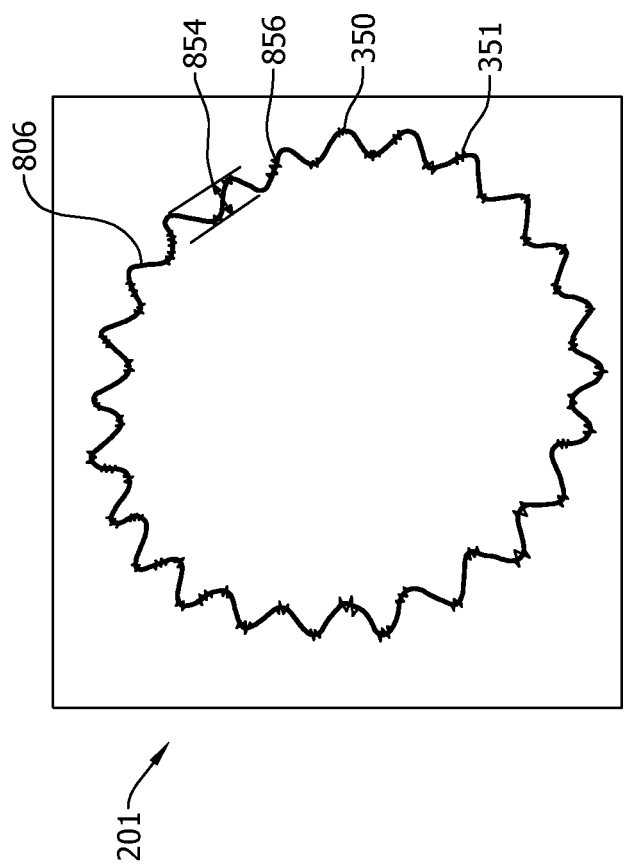
FIG. 3C shows a coil loop fabricated with a fiber conductor.

FIG. 3A shows an example RF coil assembly 302. FIG. 3B is a schematic diagram of fiber conductor 220-*f*. FIG. 3C shows a coil loop 201 of RF coil assembly 302 formed with fiber conductor 220-*f*. FIG. 3D shows coil loop 201 when being coupled on an anatomy of a subject. In the example embodiment, RF coil assembly 302 includes RF coil 304. RF coil 304 includes coil loop 201 and coupling electronics portion 203. Coil loop 201 is formed by fiber conductor 220. Fiber conductor 220 has thickness and flexibility as a thread used in sewing, and therefore may be used as a thread such as a top thread or a bottom thread in sewing. Fiber conductor 220 includes filaments 222 having an insulating coating along each individual filament 222. Example material of fiber conductor 220 is poly(p-phenylene benzobisoxazole) (PBO). Another example material of fiber conductor 220 is liquid crystal polymer (LCP) that has an electrically conductive plating, such as a silver or copper plating, over the individual filaments of the thread bundle. Fiber conductor 220 depicted in FIG. 3B is for illustration purposes only. Fiber conductor 220 may include hundred filaments wound into a conductor. The strand count and the diameter of fiber conductor 220 may vary. Filaments 222 are so fine that individual filaments 222 may be frayed from fiber conductor 220 when fiber conductor 220 is pulled along a relatively hard material such as a sewing needle. Fraying of fiber conductor 220 negatively affects the performance of fiber conductor 220 where insulation or conductivity of fiber conductor 220 is compromised when insulating coating is stripped off or filaments 222 are frayed off.

In the example embodiment, RF coil assembly 302 further includes a substrate 310. Substrate 310 is stretchable in multiple directions. In some embodiments, substrate 310 is a stretchable fabric. Coil loop 201 is coupled with substrate by stitches 806 (FIG. 3C). Stitches 806 are nonlinear, where stitches 806 include sections that are not a straight line and include turns at transition points 350. Coil loop 201 being stretchable is enabled by nonlinear stitches 806 and stretchable substrate 310 such that coil loop 201 changes the dimensions in multiple directions.

Figure 4:
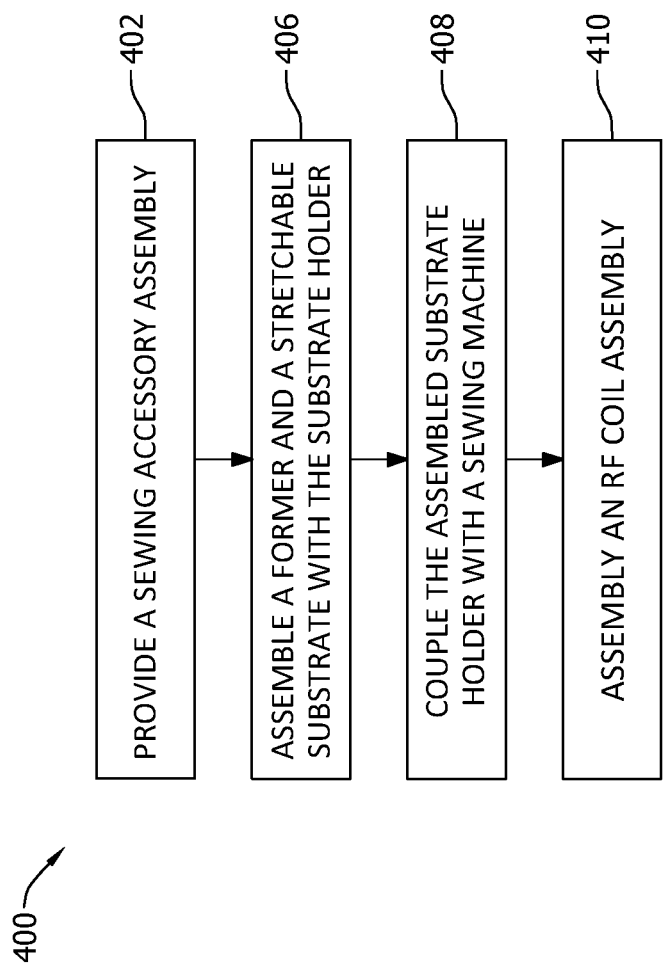
FIG. 4 is a flow chart of an example method of fabricating an RF coil assembly.

FIG. 4 is a flow chart of an example method 400 of fabricating a stretchable RF coil assembly. In the example embodiment, method 400 includes providing 402 a sewing accessory assembly. Sewing accessory assembly 250 may include a presser foot 258. Sewing accessory assembly 250 may further include one or more needles 260. Sewing accessory may also include a substrate holder 252. The elements in sewing accessory assembly 250 are configured to be coupled with a sewing machine such that at least part of the RF coil assembly is fabricated with a sewing machine.

Figure 5:
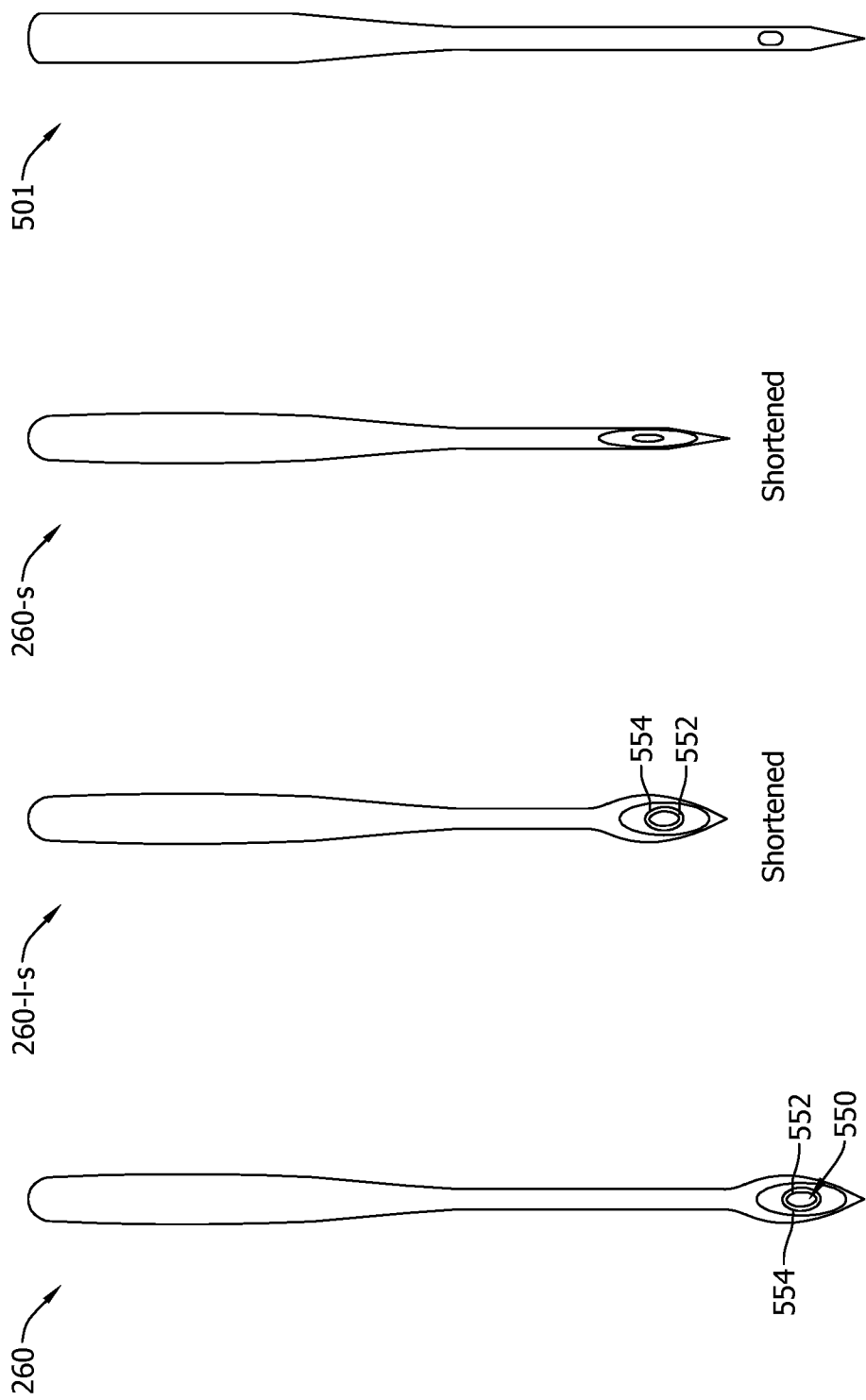
FIG. 5A shows an example needle of the sewing accessory assembly shown in FIG. 2B.
FIG. 5B shows another example needle of the sewing accessory assembly shown in FIG. 2B.
FIG. 5C shows one more example needle of the sewing accessory assembly shown in FIG. 2B.
FIG. 5D shows a known needle of a sewing machine.

FIGS. 5A-5C show example needles 260. FIG. 5D shows a typical known needle 501 of sewing machine 255. In the example embodiment, needle 260 defines an eye 550. Needle 260 may further include a lining 552 positioned along a rim 554 of eye 550. Lining 552 is fabricated with material that is relatively soft such that fiber conductor 220 does not fray when being pulling against the material. Example material is rubber, plastic, or silicon. Lining 552 may be coated along eye 550. Lining 552 may be coated via a dipping mechanism such that the end of needle 260 including eye 550 is coated with the relatively soft material. Lining 552 may be an insert that coupled with needle 260 at rim 554 via mechanisms such as adhesives. Needle 260-1-*s* also includes lining 552 along rim 554. Needle 260-*s* does not include lining 552. Compared to needle 260-1, needle 260-1-*s*, 260-*s* has a length shorter than standard sewing needles 501 of a sewing machine 255. Standard sewing needles of a sewing machine typically has the same length. Needle 260 having a reduced length is advantageous in sewing coil loops 201 with a stretchable substrate 310 and/or a former, which may have a thickness greater than the thickness of fabrics or components used in conventional sewing.

Figure 6:
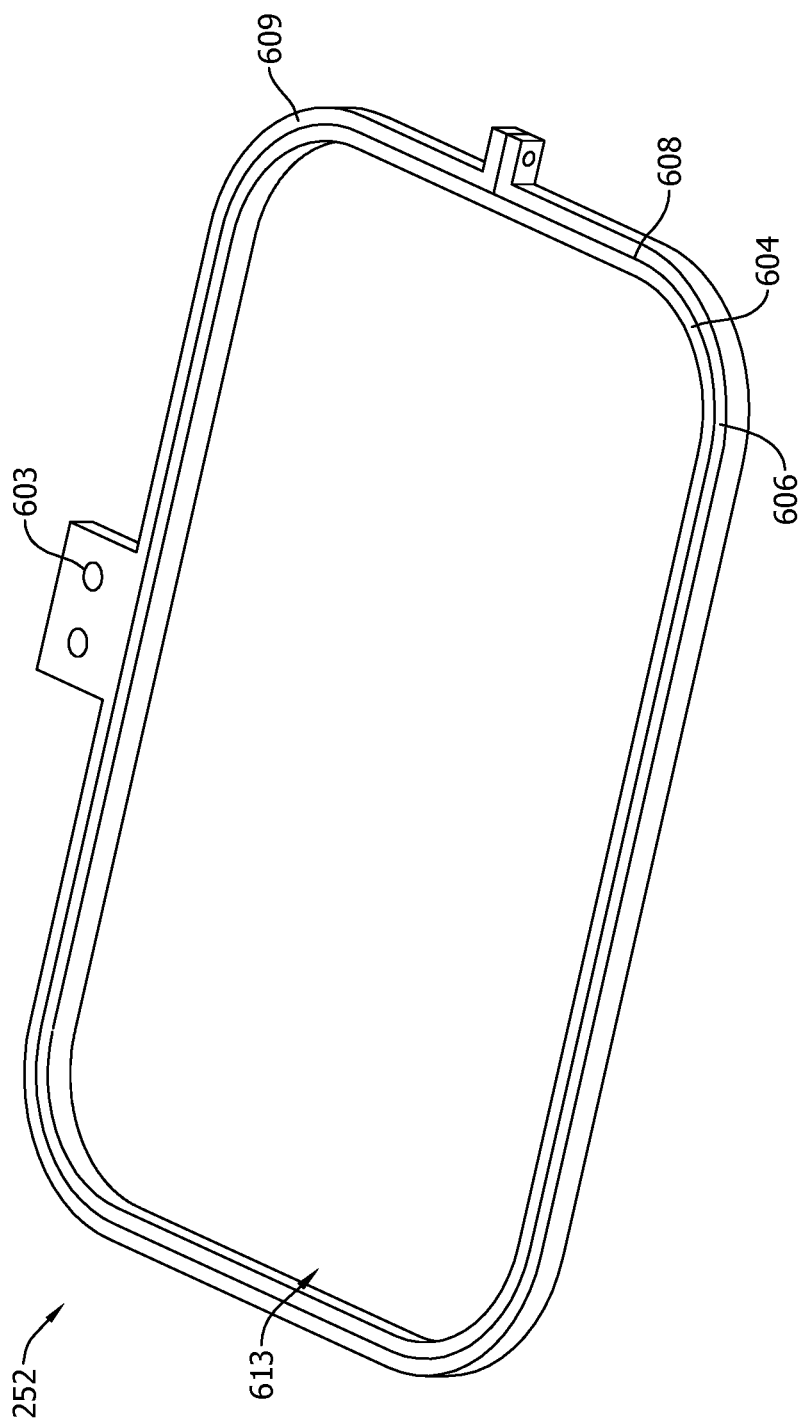
FIG. 6 shows an example substrate holder.

FIG. 6 shows an example substrate holder. In the example embodiment, substrate holder 252 is configured to fit with a sewing machine. Substrate holder 252 includes brackets 603 configured to be coupled with a hoop coupler 256 of sewing machine 255 (FIG. 2C). Substrate holder 252 has a dimension that is suitable to be used with a sewing machine. For example, substrate holder 252 may have a dimension of 28 inches (in.) (71 cm) by 15 in. (38 cm). Substrate holder 252 forms a loop 609 and defines an aperture 613 such that a fabric is held by substrate holder 252 and stretched over aperture 613. Stitches are formed on the fabric within inner hoop 606.

In the example embodiment, substrate holder 252 includes an inner hoop 604 and an outer hoop 606. Outer hoop 606 is sized to surround inner hoop 604. For example, an inner dimension of outer hoop 606 may be approximately equal to but slightly greater than an outer dimension of inner hoop 604 such that inner hoop 604 is positioned inside outer hoop 606, providing a gap 608 between inner hoop 604 and outer hoop 606 that is sized to receive a stretchable substrate 310 and/or a former therethrough. The difference in the inner dimension of outer hoop 606 and outer dimension of inner hoop 604 may be approximately equal to or smaller than thickness of substrate 310 and/or the former such that substrate 310 and/or the former is held by inner hoop 604 and outer hoop 606.

Figure 7A:
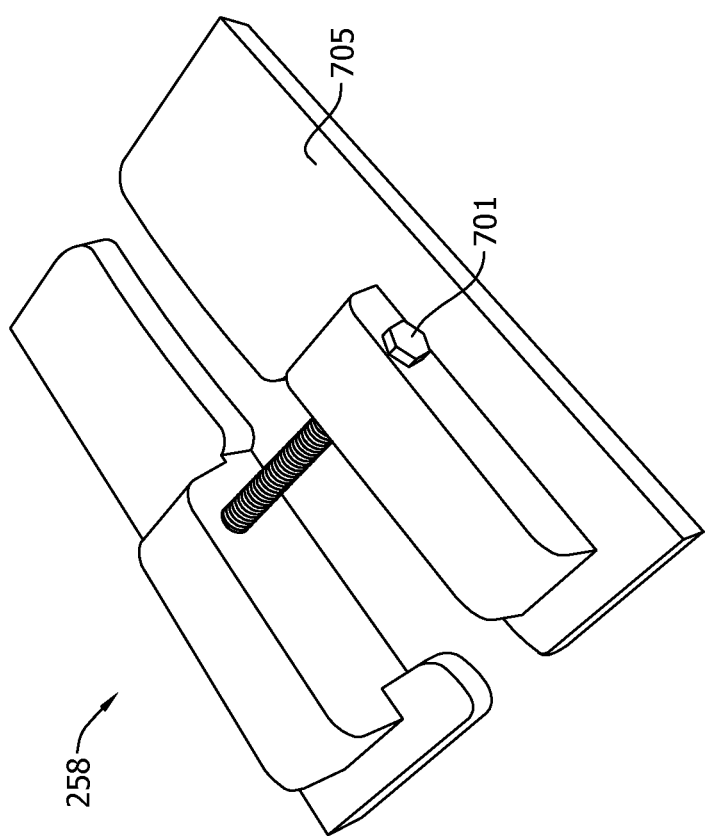
FIG. 7A is a top perspective view of an example presser foot of the sewing accessory assembly shown in FIG. 2B.
Figure 7C:
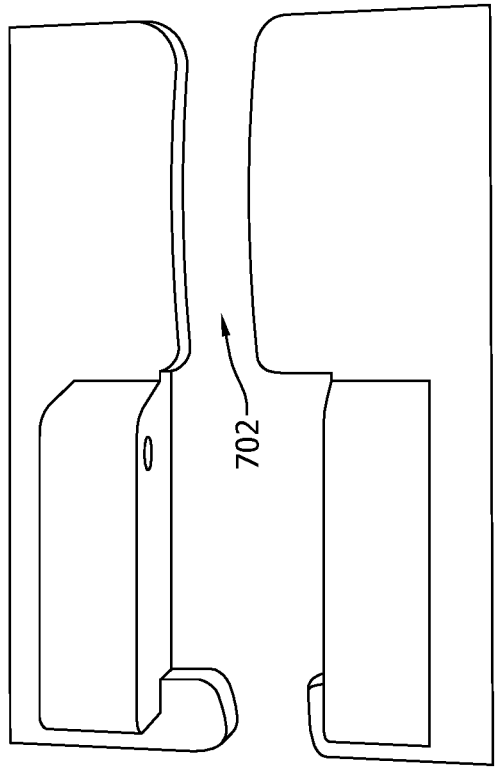
FIG. 7C is a top perspective view of the presser foot shown in FIG. 7B.
Figure 7E:
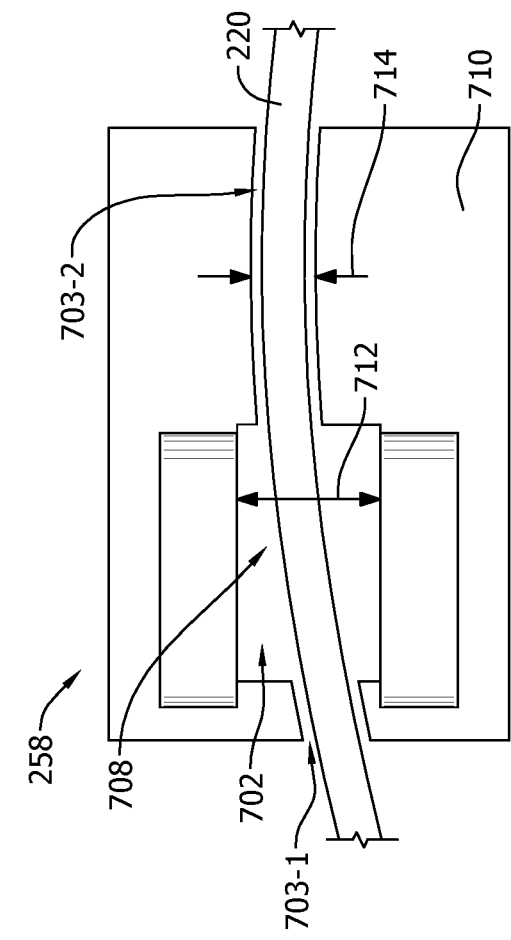
FIG. 7E is a top view of the presser foot shown in FIG. 7B with a tube placed along a channel defined by the presser foot.
Figure 7B:
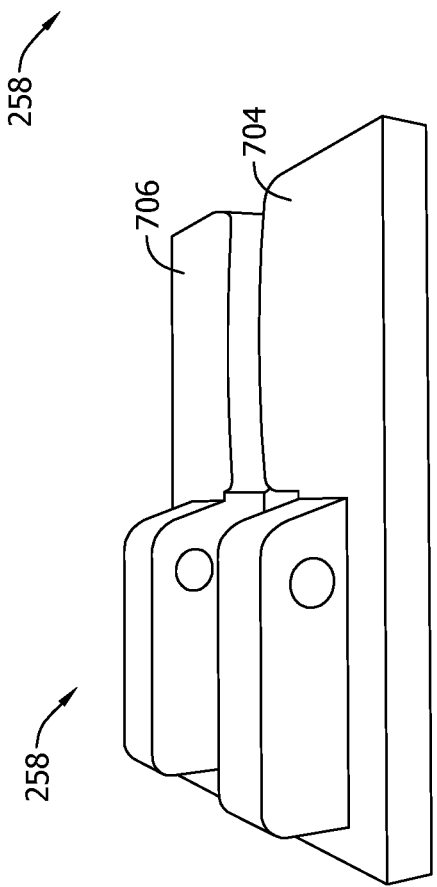
FIG. 7B is a side perspective view of the presser foot shown in FIG. 7A without depicting a pin.
Figure 7D:
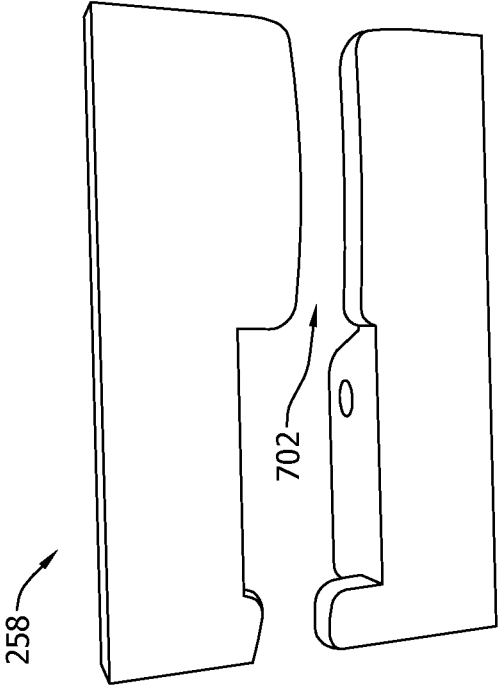
FIG. 7D is a bottom perspective view of the presser foot shown in FIG. 7B.

FIGS. 7A-7E show an example presser foot 258. FIG. 7A is a top perspective view of presser foot 258. FIGS. 7B-7E are various views of presser foot 258 without depicting a pin 701. In the example embodiment, foot body 705 of presser foot 258 defines a channel 702. Channel 702 may be curved. In some embodiments, channel 702 is straight. Foot body 705 includes a first portion 704 and a second portion 706 positioned separate from one another and define channel 702. First portion 704 and second portion 706 may be discreet pieces. In some embodiments, first portion 704 and second portion 706 are connected via an intermediate portion (not shown) and channel 702 is defined on the intermediate portion. Channel 702 is sized to receive a conductor 220 therethrough. Channel 702 includes a first end channel 703-1 and a second end channel 703-2 separated by needle aperture 708. First end channel 703-1 and second end channel 703-2 are curved in the same direction. For example, when viewed from a side 710 (FIG. 7E) of presser foot 258, first end channel 703-1 and second end channel 703-2 are both concave. As a result, the section of coil loop 201 received in channel does not change between being concave and being convex. Channel 702 further includes needle aperture 708 having a first width 712 greater than a second width 714 of the rest of channel 702. Needle aperture 708 is positioned between first end channel 703-1 and second end channel 703-2. The greater width 712 of needle aperture 708 provides space for a needle to enter through substrate 310 and for stitches to be sew around conductor 220 without needle puncturing conductor 220.

Referring back to FIG. 4, in the example embodiment, method 400 further includes assembling 406 a former and a stretchable substrate with the substrate holder. Sides of the former and substrate 310 are held between inner hoop 604 and outer hoop 606. Method 400 also includes coupling 408 the assembled substrate holder with a sewing machine. Substrate holder 252 may be placed underneath the presser foot 258. Alternatively, substrate holder 252 may be placed on a platform of the sewing machine that is underneath the needle arm 254 before presser foot 258 and/or the presser foot holder is attached to sewing machine 255. Substrate holder 252 may be coupled with embroidery hoop coupler 256 of sewing machine 255. The height of presser foot 258 may be adjusted based on the thickness of first substrate 310 and the former. During sewing, a shorter needle 260-*s*, 260-1 may be used to accommodate the thickness of substrate 310 and the former.

In the example embodiment, method 400 further includes assembling 410 RF coil loops by sewing stitches to attach the RF coil loop with the stretchable substrate. Electronics and/or cables, such as coupling electronics portion 203 and/or coil-interfacing cable 212 may be electrically coupled with RF coil loop 201.

In the example embodiment, fiber conductor 220 may be used as the sewing threads. Fiber conductor 220 may a bottom thread, where fiber conductor 220 is wound as threads in a bobbin of sewing machine 255.

In some embodiments, fiber conductor 220 is the top thread, where fiber conductor 220 is wound in a spool of fiber conductor 220. When fiber conductor 220 is used as the top thread, needle 260-1, needle 260-*s* is used to prevent fraying of fiber conductor 220 when fiber conductor 220 runs through eye 550 of needle 260 during sewing, because a sewing needle is fabricated with a relatively hard material for the purpose of sewing.

In the example embodiment, method 400 of fabricating an RF coil assembly may further include attaching a presser foot with a sewing machine. Presser foot 258 may be attached to a presser foot holder by pin 701 of presser foot 258 being snapped and received into a shank of the presser foot holder. Using presser foot 258 is advantageous in preventing fraying of fiber conductor 220-*f* or puncturing of conductor 220 by positioning conductor 220 along channel 702 of presser foot 258.

In the example embodiments, stitches 806 may be in a nonlinear pattern, where stitches 806 curve at transitioning points. The methods, systems, and assemblies described herein are advantageous over known methods of fabricating stretchable coil loops in a nonlinear pattern. The parameters of coil loops may be adjusted based on the desired level of stretchability. For example, the height 854 of curves 856 may be adjusted by adjusting stitch width. Other parameters such as the curvature of curves 856, the size of coil loop 201, and the pattern of coil loop 201 may be adjusted based on the design of coil loops 201. A pattern 262 (FIG. 2C) of coil loops may be loaded to sewing machine and the pattern is sewn by operating the sewing machine. To customize a design, only design files need to be changed and loaded to sewing machine 255. Stretching and flexing a coil loop 201 may stress anchor stitches 351 at transition points 350 and may break anchor stitches 351 over time from repeated stretching and flexing. To strengthen the coupling between coil loop 201 with substrate 310, a plurality of anchor stitches 351 may be placed at transition points 350 of stitches and at points of stitches 806 other than transition points 350 such that multiple anchor stitches 351 hold coil loop 201 in place with substrate 310. Further, fraying of fiber conductor 220-*f* is prevented using presser foot 258 having channel 702.

In the example embodiment, after stitches 806 are sewn to attach coil loop 201 with substrate 310, former is removed from RF coil assembly 302. The former may be water soluble such that the former is removed by being dissolved in water. Example material of a former is polyvinyl alcohol (PVA). The former does not produce a detectable level of proton MR signals. The performance of RF coil assemblies therefore is not affected even if the former is not completely removed from assembled RF coil loops 201. Coupling electronics portion 203 and/or coil interfacing cable 212 may be coupled with coil loops 201 after the removal of the former.

Figure 8A:
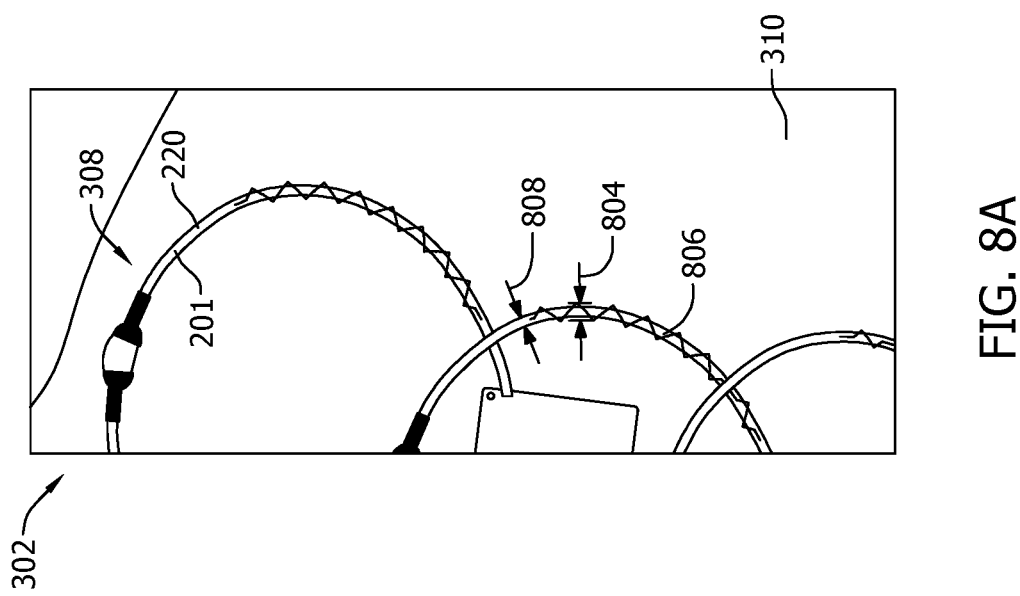
FIG. 8A shows another example RF coil assembly assembled with a substrate using the methods described herein.
Figure 8C:
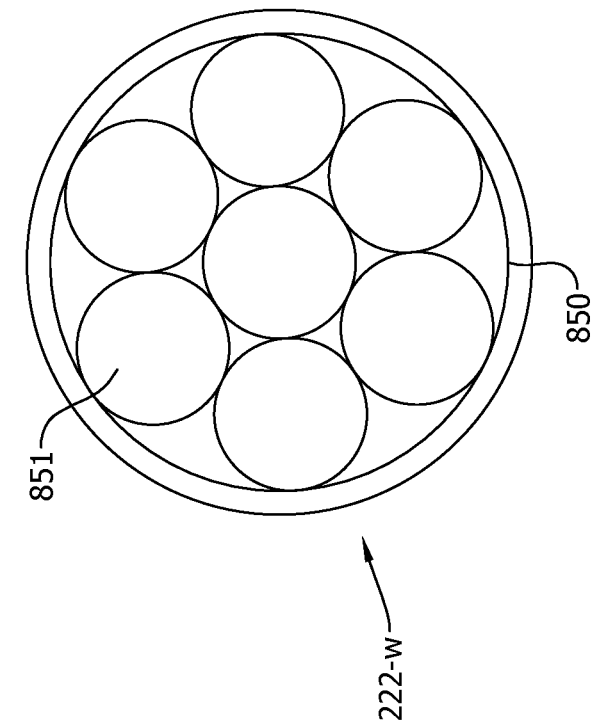
FIG. 8C is a cross-sectional view of another example wire conductor of the coil loop in the RF coil assembly shown in FIG. 8A.
Figure 8B:
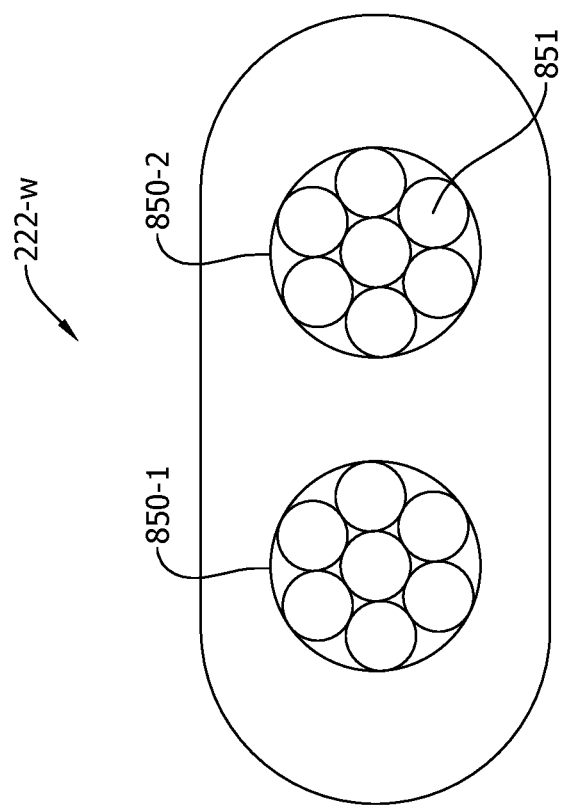
FIG. 8B is a cross-sectional view of an example wire conductor of the coil loop in the RF coil assembly shown in FIG. 8A.

FIG. 8A shows another example RF coil assembly. FIG. 8B is a cross-sectional view of an example wire conductor 220-*w* of coil loop 201. FIG. 8C is a cross-sectional view of another example wire conductor 220-*w* of coil loop 201. In the example embodiment, RF coil loop 201 is formed by wire conductor 220. Wire conductor 220-*w* is used for illustration purposes. The assemblies, systems, and methods described below in connection with FIGS. 8A-10E may be applied with fiber conductor 220 by replacing wire conductor 220-*f* with fiber conductor 220-*w*.

In the example embodiment, wire conductor 220-*w* includes a first strand group 850-1 and a second strand group 850-2. Wire conductor 220-*w* may include only one strand group 850. Strand group 850 may include one or more strands 851. Wire conductor 220 further includes dielectric material encapsulating strand group 850. RF coil loops 201 are coupled with substrate 310 using stitches 806 being sewed on substrate 310 and around RF coil loops 201. Substrate 310 may be a stretchable substrate. RF coil loop 201 includes a wire conductor 220 or a fiber conductor 220. RF coil loops 201 may be stretchable. In fabricating RF coil assemblies 302, stitches should not puncture into conductor 220, otherwise rendering RF coil loop 201 defective as the puncturing may damage insulating material of conductor 220. Further, the spatial design and overlapping between RF coil loops need to be kept according to the design of the RF coil assemblies to provide optimized performance of RF coil assemblies in terms of signal to noise ratio (SNR) and decoupling between neighboring RF coil loops 201. Known fabrication methods do not meet these needs.

Figure 9:
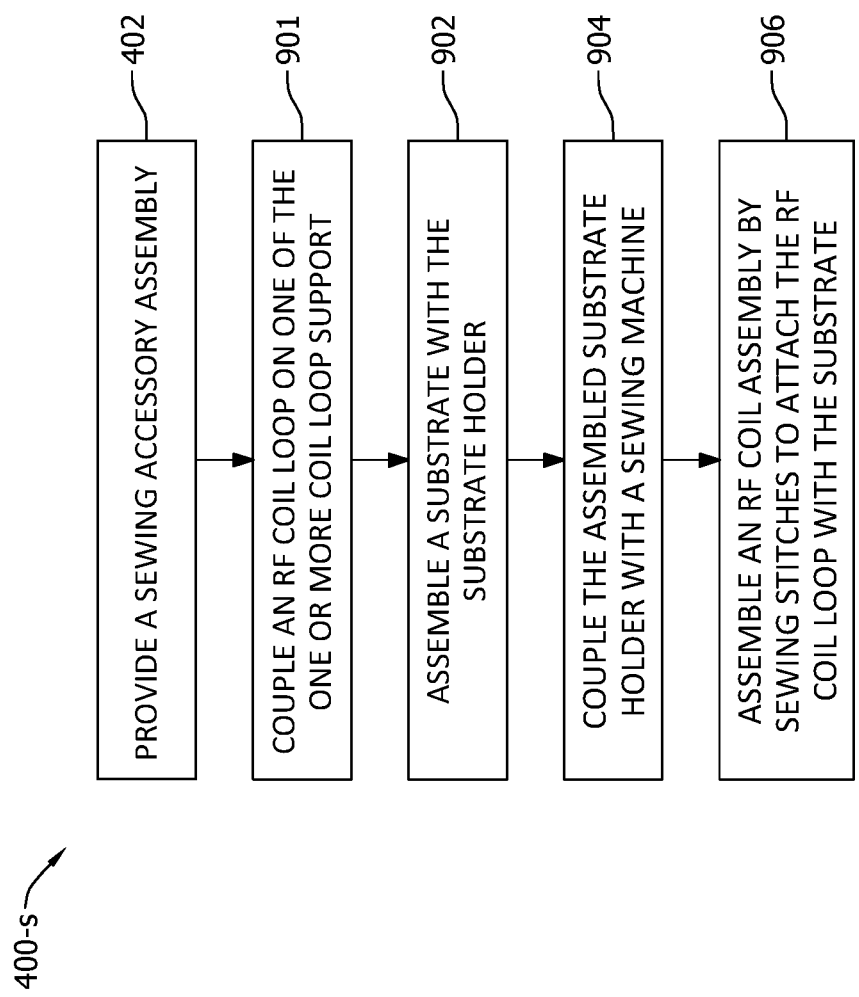
FIG. 9 is a flow chart of another example method of fabricating an RF coil assembly.

FIG. 9 is a flow chart of another example method 400-*s* of fabricating an RF coil assembly. Method 400-*s* includes providing 402 a sewing accessory assembly. Sewing accessory assembly 250 may include a presser foot 258 (FIGS. 7A-7E).

Figure 10A:
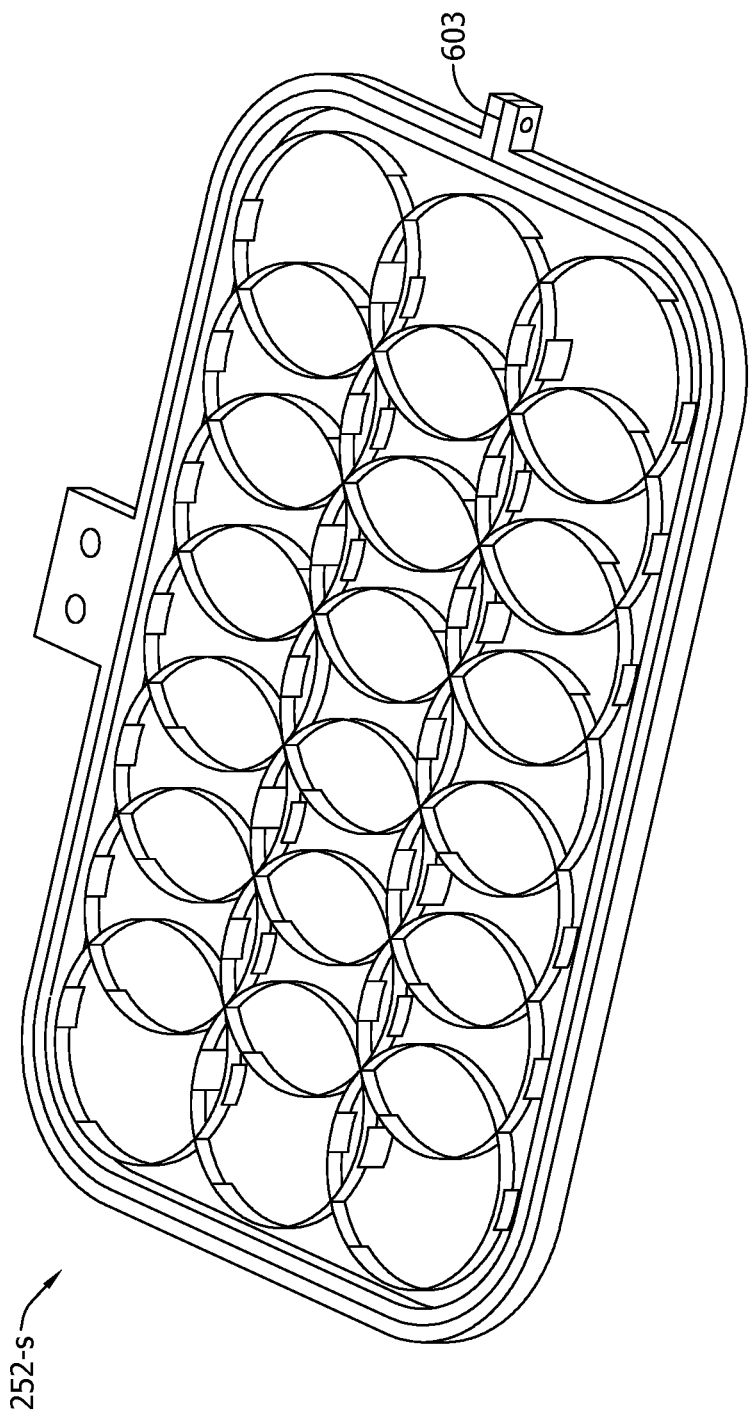
FIG. 10A is a perspective view of another example substrate holder of the sewing accessory assembly shown in FIG. 2B.
Figures 10B, 10C:
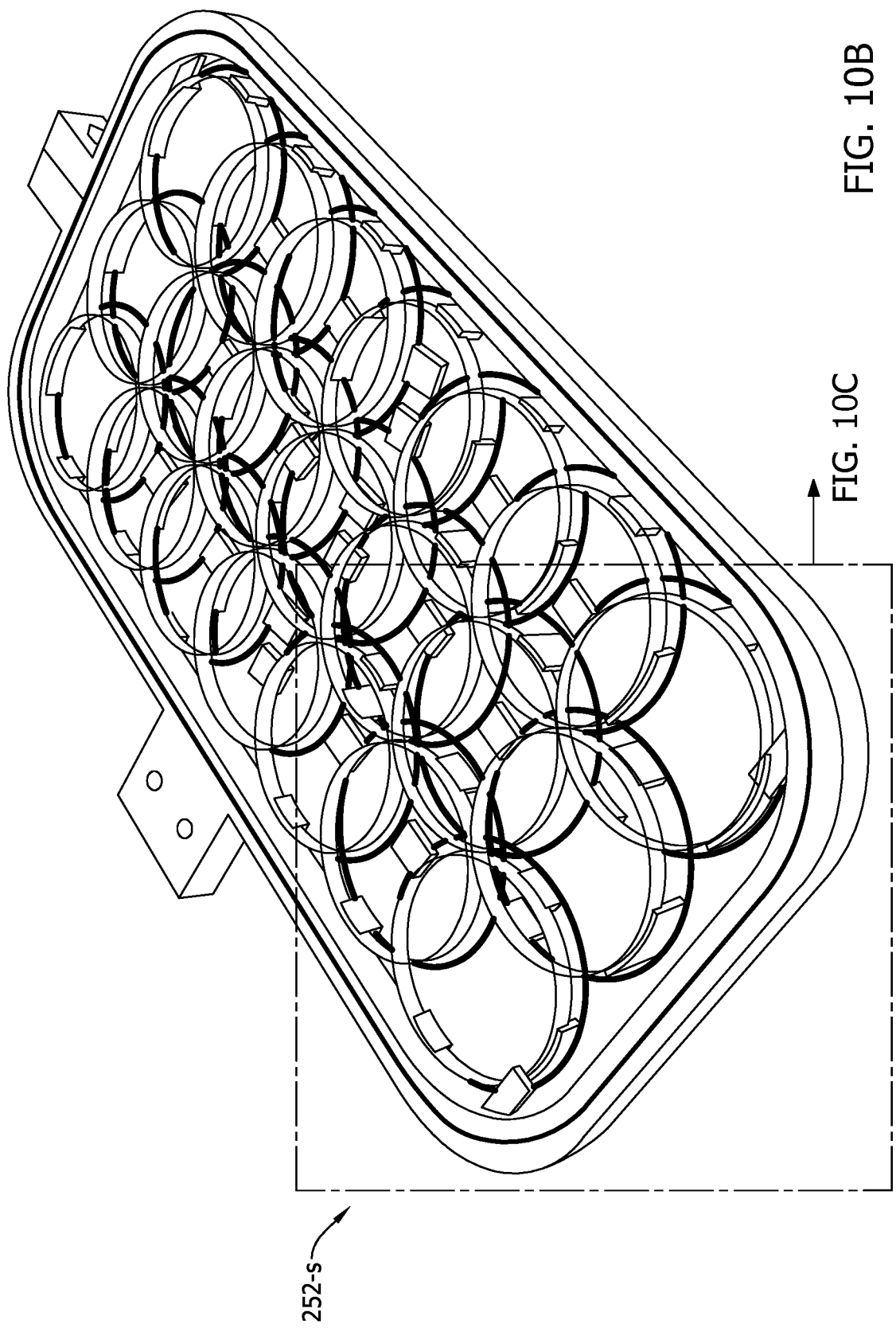
FIG. 10B is a perspective view of the substrate holder shown in FIG. 10A coupled with RF coil loops.
FIG. 10C is an enlarged view of a section of the substrate holder shown in FIG. 10B.
Figure 10C:
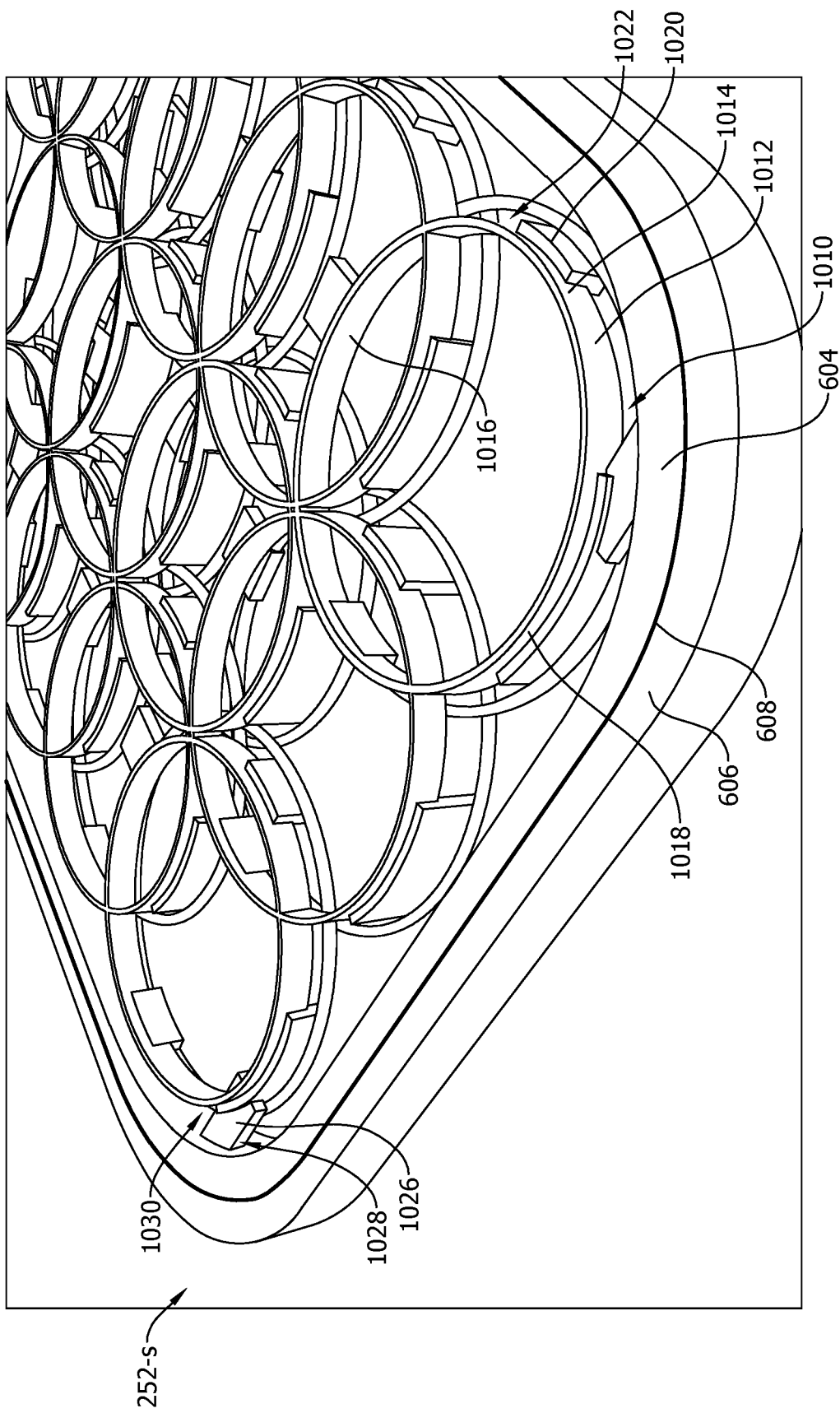
Figure 10D:
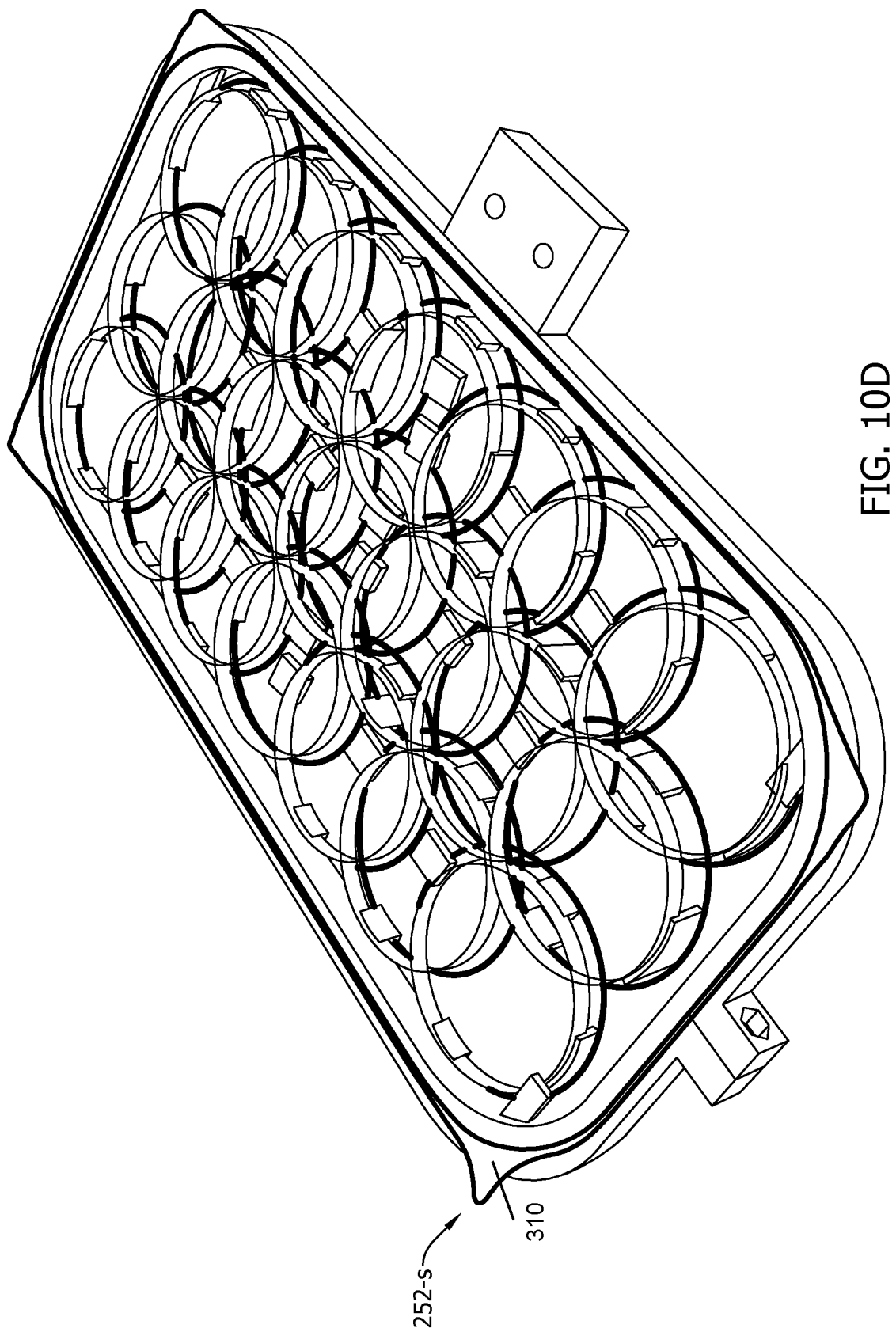
FIG. 10D is a perspective view of the substrate holder shown in FIG. 10B further coupled with a substrate.
Figure 10E:
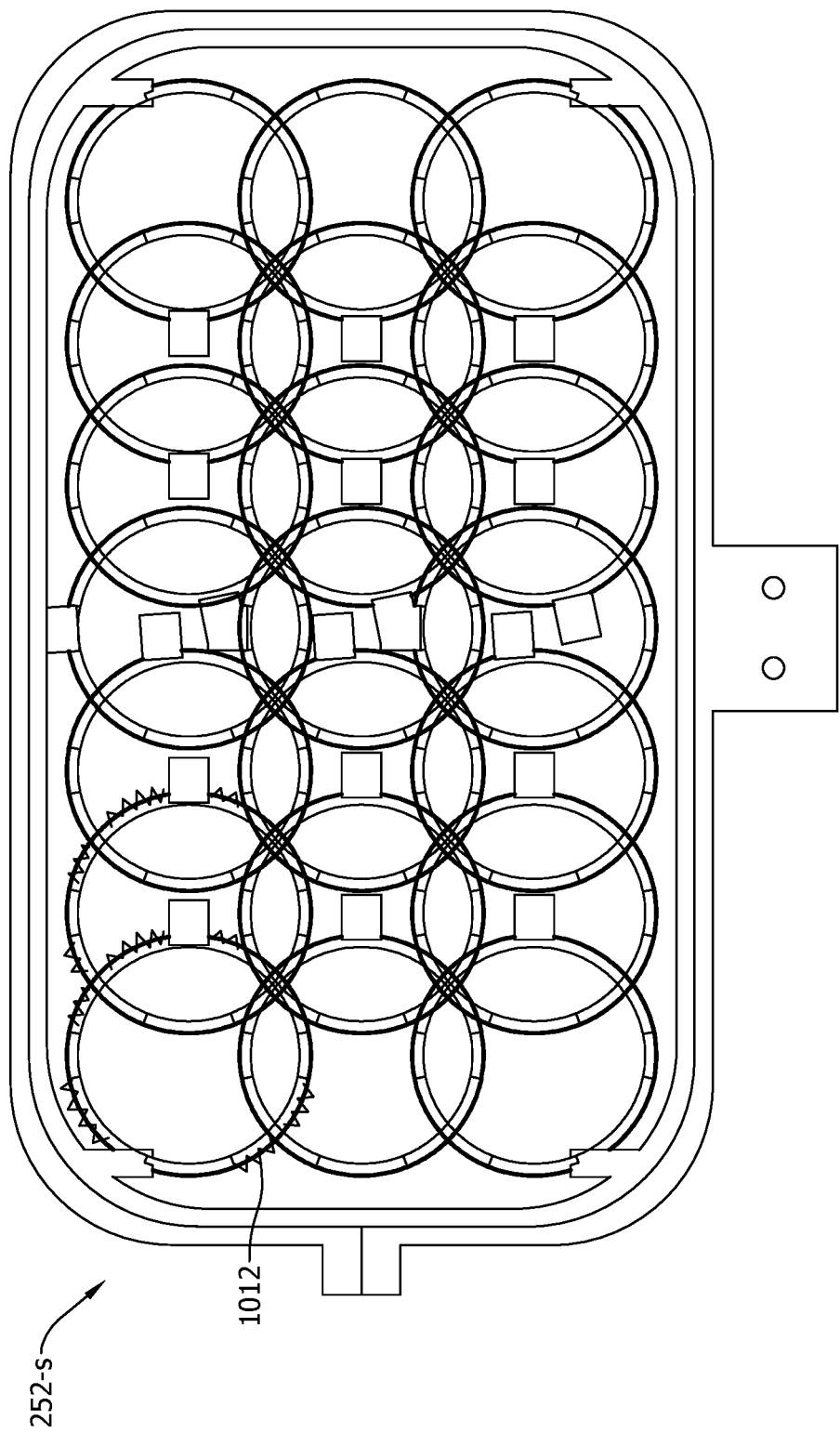
FIG. 10E is a schematic diagram illustrating RF coils are assembled using the method shown in FIG. 9.

FIGS. 10A-10F show another example substrate holder 252-*s*. FIG. 10A is a perspective view of substrate holder 252-*s*. FIG. 10B is a perspective view of substrate holder 252 coupled with coil loops 201. FIG. 10C is an enlarged view of a section in FIG. 10B. FIG. 10D shows a substrate 310 is coupled in substrate holder 252. FIG. 10E shows stitches 806 are sewn on coil loops 201.

In the example embodiment, substrate holder 252-*s* includes a bracket 603 configured to couple with a embroidery hoop coupler 256 of sewing machine 255. Compared to substrate holder 252 shown in FIG. 6, substrate holder 252-*s* includes coil loop supports 1010. Coil loop supports 1010 are configured to receive coil loops 201 thereon. Coil loop support 1010 includes a support body 1012 and forms a loop 1014. Loop 1014 may be circular. Coil loop support 1010 may be in other shapes, such as rectangular or polygonal, in which shapes coil loops 201 are in RF coil assembly 302. Support body 1012 includes an inner surface 1016 and an outer surface 1018 positioned opposite from inner surface 1016. Coil loop support 1010 may include protrusions 1020 positioned on the outer surface 1018. Protrusions 1020 extend outward from loop 1014 such that a gap 1022 is provided when coil loop 201 is coupled with coil loop support 1010 (see FIG. 10C). Gap 1022 provides space for stitches 806 to be sewn around coil loop 201. The pattern of coil loop supports 1010 is based on the pattern of coil loops 201 of RF coil assembly 302 such that when coil loops 201 are coupled with coil loop supports 1010, the layout of coil loops 201 is according to the pattern designed for RF coil assembly 302. Further, coil loop supports 1010 provide support to substrate 310, reducing sagging from the tucking and pulling of needle 260. For example, coil loop supports 1010 provide support to substrate 310 such that areas away from inner hoop 604 do not suffer from more sagging than areas proximate to inner hoop 604. As a result, a former configured to reducing sagging in the center area may be eliminated in fabricating RF coil assemblies.

In the example embodiment, coil loop supports 1010 are coupled with inner hoop 604. Coil loop supports 1010 may be coupled with inner hoop 604 via a connector 1026. Connector 1026, coil loop supports 1010, and inner hoop 604 may be integrally fabricated as one single piece or having only one piece. Alternatively, coil loop supports 1010 are removably coupled with inner hoop 604. For example, inner hoop 604 defines apertures 1028 sized to receive connector 1026 therein. In another example, coil loop supports define a slot 1030 sized to receive connector 1026. Removably couplable coil loop supports 1010 enable changes of the designs of coil loops 201 in RF coil assembly 302 by replacing coil loop supports 1010.

In operation, coil loops 201 are coupled with coil loop supports 1010. Substrate 310 may a stretchable fabric. Substrate 310 is placed over coil loops 201. In some embodiment, a former (not shown) is placed further over substrate 310 configured to reduce sagging of substrate 310 or deformation of substrate 310 during sewing. Outer hoop 606 is then placed over substrate 310 and/or former such that sides of substrate 310 and/or former are held between inner hoop 604 and outer hoop 606. The assembled substrate holder 252 is flipped over such that coil loops are facing an operator during sewing. The assembled substrate holder 252 is coupled with embroidery hoop coupler 256 of sewing machine. Stitches 806 may be applied at desired locations on coil loops 201.

In the example embodiment, coupling electronics portions 203 may have been coupled with coil loops 201 before sewing. Alternatively, coupling electronics portions 203 are coupled with coil loops after sewing.

Referring back to FIG. 9, in the example embodiment, method 400-*s* includes positioning 901 an RF coil loop on one of the one or more coil loop support. Method 400 further includes assembling 902 a substrate with a substrate holder by securing the substrate between the inner hoop and outer hoop. In some embodiments, a former is placed over the substrate to further reduce deformation or sagging of the substrate during sewing from the pulling and tucking of the needle, due to limited tension provided by the inner hoop and the outer hoop. Method 400 further includes coupling 904 the assembled substrate holder with a sewing machine. For example, assembled substrate holder 252 is coupled with sewing machine 255 by coupling bracket 603 with embroidery hoop coupler 256 of sewing machine 255. The height of a presser foot or the height of needle 260 of sewing machine 255 may be adjusted based on the thickness of coil loop 201, substrate 310, and/or the former. An RF coil assembly is assembled 906 by sewing stitches to attach RF coil loops 201 of the RF coil assembly 302 with the substrate. Presser foot 258 may be used to hold conductor 220 in place to prevent conductor 220 being punctured by needle 260. Stitches 806 may be zigzag stiches (FIG. 8A). A width 804 of stitches 806 is adjustable to accommodate the width 808 of conductor 220. Curvature of curved channel 1002 may be adjusted to accommodate the curvature of coil loop 201 in RF coil assembly. If a former is used, former is removed from RF coil assembly 302. The former may be water soluble such that the former is removed by being dissolved in water. Example material of a former is PVA. The former does not produce a detectable level of proton MR signals. The performance of RF coil assemblies therefore is not affected even if the former is not completely removed. Coupling electronics portion 203 may be coupled with coil loops 201 after the removal of the former.

At least one technical effect of the systems and methods described herein includes (a) automized and customized methods of fabricating RF coil assemblies using a sewing machine; (b) presser feet of a sewing machine for fabricating RF coil assemblies; (c) substrate holders configured to hold substrate of RF coils and to couple with a sewing machine like an embroidery hoop; and (d) needles for fabricating RF coil assemblies.

Example embodiments of assemblies, systems, and methods of fabricating RF coil assemblies are described above in detail. The systems and methods are not limited to the specific embodiments described herein but, rather, components of the systems and/or operations of the methods may be utilized independently and separately from other components and/or operations described herein. Further, the described components and/or operations may also be defined in, or used in combination with, other systems, methods, and/or devices, and are not limited to practice with only the systems described herein.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method of fabricating a radio-frequency (RF) coil assembly of a magnetic resonance (MR) system using a sewing machine, comprising:
   providing a sewing accessory assembly, the sewing accessory assembly including a substrate holder, the substrate holder including:
      an inner hoop;
      one or more coil loop supports configured to be coupled with the inner hoop and be positioned within the inner hoop; and
      an outer hoop;
   coupling an RF coil loop with one of the one or more coil loop supports;
   assembling a substrate with the substrate holder by:
      securing the substrate between the inner hoop and the outer hoop;
   coupling the assembled substrate holder with a sewing machine; and
   assembling an RF coil assembly by:
      sewing stitches to attach the RF coil loop with the substrate.

2. The method of claim 1, wherein the sewing accessory assembly further includes a presser foot, the presser foot defines a channel, wherein:
   sewing stitches further comprises positioning the RF coil loop along the channel during sewing.

3. The method of claim 2, wherein the channel is curved.

4. The method of claim 1, wherein assembling a substrate further comprises:
   assembling a former and the substrate with the substrate holder by:
      securing the former and the substrate between the inner hoop and the outer hoop.

5. The method of claim 4, wherein the former is soluble in water, the method further comprising:
   removing the former from the RF coil assembly by:
      dissolving the former using water.

6. A method of fabricating a stretchable radio-frequency (RF) coil assembly of a magnetic resonance (MR) system using a sewing machine, comprising:
   providing a sewing accessory assembly, the sewing accessory assembly including:
      a substrate holder including an inner hoop and an outer hoop;
   assembling a former and a stretchable substrate with the substrate holder by:
      coupling sides of the former and sides of the stretchable substrate between the inner hoop and the outer hoop;
   coupling the assembled substrate holder with a sewing machine; and
   assembling an RF coil assembly by:
      sewing a pattern of a fiber conductor on the stretchable substrate.

7. The method of claim 6, wherein the sewing accessory assembly further includes:
   a needle defining an eye, the needle further including a lining positioned around the eye and configured to reduce fraying of the fiber conductor.

8. The method of claim 7, wherein assembling an RF coil assembly further comprises:
   loading a spool wound with the fiber conductor to the sewing machine;
   coupling the needle with the sewing machine;
   threading the fiber conductor through the eye of the needle; and
   sewing the pattern of the fiber conductor by sewing the fiber conductor as a top thread.

9. The method of claim 6, wherein assembling an RF coil assembly further comprises:
   loading a bobbin wound with the fiber conductor to the sewing machine; and
   sewing the pattern of the fiber conductor by sewing the fiber conductor as a bottom thread.

10. The method of claim 6, wherein the sewing accessory assembly further includes a presser foot, the presser foot defining a channel, and assembling an RF coil assembly further comprises:

coupling the presser foot with the sewing machine; and
sewing the pattern of the fiber conductor by positioning the fiber conductor along the channel.

11. The method of claim 10, wherein the channel is curved.

12. The method of claim 6, wherein the sewing accessory assembly further includes:
a needle having a reduced length from a standard needle of the sewing machine,
wherein assembling the RF coil assembly further comprises:
sewing the pattern using the needle.

13. The method of claim 6, wherein assembling an RF coil assembly further comprises:
sewing nonlinear stitches of the fiber conductor on the stretchable substrate.

14. The method of claim 13, wherein assembling an RF coil assembly further comprises:
adjusting parameters of the nonlinear stitches.

15. The method of claim 13, wherein sewing nonlinear stitches further comprises:
sewing a plurality of anchor stitches at transition points of the nonlinear stitches and at points of the nonlinear stitches other than the transition points.

16. The method claim 6, wherein assembling an RF coil assembly further comprises:
customizing the pattern of the fiber conductor;
loading the customized pattern to the sewing machine; and
operating the sewing machine such that a presser foot moves according to the customized pattern.

17. A sewing accessory assembly of a sewing machine for fabricating a radio-frequency (RF) coil assembly of a magnetic resonance (MR) system, comprising:
a needle defining an eye, the needle further comprising a lining positioned around the eye and configured to reduce fraying of a fiber conductor.

18. The sewing accessory assembly of claim 17, wherein the needle has a length shorter than a standard needle of a sewing machine.

19. The sewing accessory assembly of claim 17, further comprising a substrate holder, wherein the substrate holder comprises:
an inner hoop;
one or more coil loop supports configured to be coupled with the inner hoop and be positioned within the inner hoop; and
an outer hoop sized to surround the inner hoop.

20. The sewing accessory assembly of claim 17, further comprises a presser foot, the presser foot defining a curved channel.

* * * * *